United States Patent [19]

Koda et al.

[11] Patent Number: 4,581,372
[45] Date of Patent: Apr. 8, 1986

[54] SULFONIUM COMPOUNDS

[75] Inventors: Akihide Koda; Mikio Hori, both of Gifu; Mitsugi Yasumoto, Tokushima; Ichiro Yamawaki, Tokushima; Yuji Yamada, Tokushima; Katsuo Takikawa, Naruto, all of Japan

[73] Assignee: Taiho Pharmaceutical Company Limited, Tokyo, Japan

[21] Appl. No.: 541,799

[22] Filed: Oct. 14, 1983

Related U.S. Application Data

[60] Continuation of Ser. No. 343,293, Jan. 27, 1982, abandoned, which is a division of Ser. No. 231,126, Feb. 3, 1981, Pat. No. 4,340,543.

[30] Foreign Application Priority Data

Feb. 15, 1980 [JP] Japan .................................. 55-18385
Jan. 21, 1981 [JP] Japan .................................. 56-8500

[51] Int. Cl.$^4$ ...................... A61K 31/35; A61K 31/34
[52] U.S. Cl. .................................... 514/451; 514/461
[58] Field of Search ................ 424/283, 285; 514/451, 514/461

[56] References Cited

U.S. PATENT DOCUMENTS 2,562,042  7/1951  Kipnis ............................. 260/345.1
3,455,956  7/1969  Hirano et al. ..................... 260/347.2

OTHER PUBLICATIONS

Rutter, Jr., JACS, 73, 5905 (1951).

Primary Examiner—Jerome D. Goldberg
Attorney, Agent, or Firm—Murray and Whisenhunt

[57] ABSTRACT

Sulfonium compounds represented by the formula

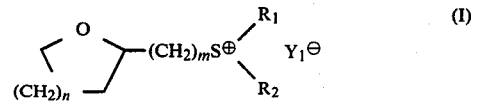

having immunostimulant activity and useful as the active components of drugs and agricultural chemicals.

18 Claims, No Drawings

SULFONIUM COMPOUNDS

This application is a continuation application of Ser. No. 343,293, filed Jan. 27, 1982, now abandoned, which is a divisional application of Ser. No. 231,126, filed Feb. 3, 1981, now U.S. Pat. No. 4,340,543.

This invention relates to novel sulfonium compounds, a process for preparing the compounds, pharmacological compositions containing such compounds and a therapeutic method with use of such compositions.

The sulfonium compounds of this invention are represented by the formula

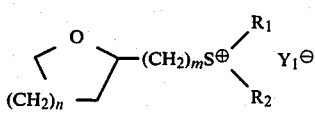 (I)

wherein $R_1$ and $R_2$ are each alkyl, cycloalkyl, cyclopropylmethyl, alkylene-2-tetrahydrofuranyl, alkylene-2-tetrahydropyranyl, alkenyl, phenyl which may be substituted with alkyl, alkoxy or halogen, aralkyl which may be substituted with alkyl, alkoxy or halogen on the benzene ring, or benzoyloxyethyl, $Y_1$ is halogen, or an inorganic acid residue or organic acid residue, n is 1 or 2, and m is an integer of 1 to 15.

Preferable examples of alkyl groups represented by $R_1$ and $R_2$ of the formula (I) are straight-chain or branched-chain alkyl groups having 1 to 10 carbon atoms, such as methyl, ethyl, propyl, isopropyl, butyl, sec-butyl, tert-butyl, pentyl, hexyl, octyl and decyl.

Preferable examples of the cycloalkyl groups represented by $R_1$ and $R_2$ of the formula (I) are those having 4 to 8 carbon atoms, such as cyclobutyl, cyclopentyl, cyclohexyl and cyclooctyl.

Preferable examples of the alkylene groups constituting the alkylene-2-tetrahydrofuranyl and alkylene-2-tetrahydropyranyl groups represented by $R_1$ and $R_2$ of the formula (I) are those having 1 to 6 carbon atoms, such as methylene, ethylene, propylene, trimethylene, tetramethylene and hexamethylene.

Preferable examples of the alkenyl groups represented by $R_1$ and $R_2$ of the formula (I) are those having 2 to 10 carbon atoms, such as vinyl, allyl, propenyl, butenyl, hexenyl, octenyl and decenyl.

Preferable examples of the aralkyl groups represented by $R_1$ and $R_2$ of the formula (I) are those in which the alkyl portion has 1 to 4 carbon atoms, such as benzyl, phenethyl and phenylpropyl. Such aralkyl groups and the phenyl group represented by $R_1$ and $R_2$ of the formula (I) may have one or more substituents on the benzene ring. Examples of preferred substituents are alkyl groups having 1 to 4 carbon atoms, such as methyl, ethyl, propyl and isopropyl, alkoxy groups having 1 to 4 carbon atoms, such as methoxy, ethoxy, propoxy and isopropoxy, and halogen atoms, such as chlorine, bromine and iodine. Examples of preferred phenyl and aralkyl groups having such substituents are o-methylphenyl, p-ethylphenyl, p-methoxyphenyl and m-chlorophenyl, and o-methylbenzyl, o-ethoxybenzyl, m-chlorobenzyl, p-bromobenzyl, o-methylphenethyl, p-chlorophenylpropyl, p-methylphenylpropyl and p-methoxyphenylbutyl.

Preferable examples of the groups represented by $Y_1$ are halogen, inorganic protonic acid residues and organic protonic acid residues. Examples of useful halogen are chlorine, iodine and bromine. Examples of useful inorganic protonic acid residues are nitrate, sulfonate, phosphate, metaphosphate and perchlorate. Exemplary of organic protonic acid residues are organic sulfonic acid residues and carboxylic acid residues. Examples of preferred organic sulfonic acid residues are p-toluenesulfonate, picrylsulfonate, cyclohexylsulfamate, camphorsulfonate, benzenesulfonate, 1,5-naphtalenedisulfonate, flavianate and methanesulfonate. Examples of preferred carboxylic acid residues are maleate, malonate, fumarate, citrate, lactate, tartrate, ascorbate, linolate, laurate, palmitate, stearate, oleate, acetate, propionate, butyrate, isobutyrate, valerate, oxalate, succinate, benzoate, nicotinate and glycyrrhizate.

Of the compounds of the formula (I), preferable are those in which at least one of the groups $R_1$ and $R_2$ is an alkyl. Especially preferable are those in which m is an integer of 1 to 5, $R_1$ and $R_2$ are each alkyl, and $Y_1$ is an organic sulfonic acid residue.

Table 1 shows preferable examples of the compounds of this invention prepared in Examples given later. In Table 1, Ts, Pic and GL in the column for $Y_1$ represent p-toluenesulfonate, picrylsulfonate and glycyrrhizate, respectively.

TABLE 1

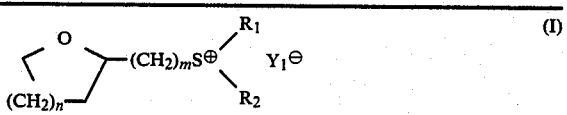 (I)

| Comp. No. | n | m | $R_1$ | $R_2$ | $Y_1$ |
|---|---|---|---|---|---|
| 1 | 1 | 1 | $CH_3$ | $CH_3$ | Ts |
| 2 | 1 | 1 | $CH_3$ | $CH_3$ | Pic |
| 3 | 1 | 1 | $CH_3$ | $CH_3$ | I |
| 4 | 1 | 1 | $CH_3$ | $CH_3$ | 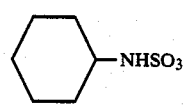—NHSO$_3$ |
| 5 | 1 | 1 | $CH_3$ | $CH_3$ | 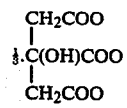 |

TABLE 1-continued $$\text{(I)} \quad \underset{(CH_2)_n}{\overset{O}{\diagdown}} CH-(CH_2)_m S^{\oplus} \overset{R_1}{\underset{R_2}{\diagdown}} Y_1^{\ominus}$$

| Comp. No. | n | m | R₁ | R₂ | Y₁ |
|---|---|---|---|---|---|
| 6 | 1 | 1 | CH₃ | CH₃ | CH₃CH(OH)COO |
| 7 | 1 | 1 | CH₃ | CH₃ | ½·H₂C(COO)(COO) |
| 8 | 1 | 1 | CH₃ | CH₃ | ½·HO—CHCOO / HO—CHCOO |
| 9 | 1 | 1 | CH₃ | CH₃ | ½·CHCOO ‖ CHCOO |
| 10 | 1 | 1 | CH₃ | CH₃ | H₂PO₄ |
| 11 | 1 | 1 | CH₃ | CH₃ | GL |
| 12 | 1 | 1 | CH₃ | n-C₄H₉ | Ts |
| 13 | 1 | 1 | CH₃ | n-C₄H₉ | Pic |
| 14 | 1 | 1 | CH₃ | n-C₁₀H₂₁ | Ts |
| 15 | 1 | 1 | CH₃ | n-C₁₀H₂₁ | Pic |
| 16 | 1 | 1 | CH₃ | n-C₁₀H₂₁ | I |
| 17 | 1 | 1 | iso-C₃H₇ | n-C₃H₇ | Ts |
| 18 | 1 | 1 | n-C₃H₇ | n-C₆H₁₃ | Ts |
| 19 | 1 | 1 | CH₃ | cyclopentyl | Ts |
| 20 | 1 | 1 | CH₃ | cyclopentyl | Pic |
| 21 | 1 | 1 | CH₃ | phenyl | Ts |
| 22 | 1 | 1 | CH₃ | phenyl | Pic |
| 23 | 1 | 1 | CH₃ | CH₂-phenyl | Ts |
| 24 | 1 | 1 | CH₃ | CH₂-phenyl | Pic |
| 25 | 1 | 1 | CH₂-phenyl | CH₂-phenyl | Ts |
| 26 | 1 | 1 | CH₂-phenyl | CH₂-phenyl | Pic |

TABLE 1-continued $$\underset{(CH_2)_n}{\overset{O}{\diagdown}}\!\!\!-(CH_2)_m S^{\oplus}\!\!\!<\!\!\!\overset{R_1}{\underset{R_2}{}} Y_1^{\ominus} \qquad (I)$$

| Comp. No. | n | m | R₁ | R₂ | Y₁ |
|---|---|---|---|---|---|
| 27 | 1 | 1 | CH₃ | 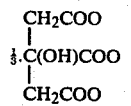 C₂H₄OCO—⟨phenyl⟩ | Ts |
| 28 | 1 | 1 | CH₃ | C₂H₄OCO—⟨phenyl⟩ | Pic |
| 29 | 1 | 2 | CH₃ | CH₃ | Ts |
| 30 | 1 | 2 | CH₃ | CH₃ | Cl |
| 31 | 1 | 2 | CH₃ | CH₃ | I |
| 32 | 1 | 2 | CH₃ | CH₃ | ⅓·CH₂COO–C(OH)COO–CH₂COO |
| 33 | 1 | 2 | CH₃ | CH₃ | CH₃CHCOO OH |
| 34 | 1 | 2 | CH₃ | CH₃ | ½·H₂C(COO)₂ |
| 35 | 1 | 2 | CH₃ | CH₃ | ½·CHCOO‖CHCOO |
| 36 | 1 | 2 | CH₃ | CH₃ | H₂PO₄ |
| 37 | 1 | 2 | CH₃ | CH₃ | ⟨cyclohexyl⟩—NHSO₃ |
| 38 | 1 | 2 | CH₃ | CH₃ | GL |
| 39 | 1 | 2 | CH₃ | n-C₄H₉ | Pic |
| 40 | 1 | 2 | CH₃ | n-C₄H₉ | Ts |
| 41 | 1 | 2 | n-C₃H₇ | n-C₈H₁₇ | Ts |
| 42 | 1 | 2 | CH₃ | sec-C₄H₉ | Ts |
| 43 | 1 | 2 | CH₃ | sec-C₄H₉ | Pic |
| 44 | 1 | 2 | CH₃ | tert-C₄H₉ | Ts |
| 45 | 1 | 2 | CH₃ | C₂H₄—⟨2-methylphenyl⟩ | Ts |
| 46 | 1 | 3 | CH₃ | CH₃ | Ts |
| 47 | 1 | 3 | CH₃ | CH₃ | ⟨pyridyl⟩—COO |
| 48 | 1 | 3 | C₂H₅ | CH₂—⟨3-chlorophenyl⟩ | Ts |

TABLE 1-continued $$\text{(CH}_2)_n\text{-CH-(CH}_2)_m\text{-S}^{\oplus}\begin{array}{c}R_1\\R_2\end{array} Y_1^{\ominus} \quad (I)$$
(with tetrahydrofuran ring containing O)

| Comp. No. | n | m | R₁ | R₂ | Y₁ |
|---|---|---|---|---|---|
| 49 | 1 | 3 | $C_2H_5$ | $CH_2$-(3-chlorophenyl) | Pic |
| 50 | 2 | 1 | $CH_3$ | $CH_3$ | Ts |
| 51 | 2 | 1 | $CH_3$ | $CH_3$ | nicotinate (pyridine-3-COO) |
| 52 | 2 | 1 | $C_2H_5$ | $C_2H_5$ | Ts |
| 53 | 2 | 1 | $C_2H_5$ | $C_2H_5$ | Pic |
| 54 | 2 | 1 | $C_2H_5$ | cyclohexyl | Ts |
| 55 | 2 | 1 | $C_2H_5$ | cyclohexyl | Pic |
| 56 | 2 | 1 | $C_2H_5$ | $CH_2CH=CH_2$ | Ts |
| 57 | 2 | 1 | $C_2H_5$ | $CH_2CH=CH_2$ | Pic |
| 58 | 2 | 2 | $CH_3$ | $CH_3$ | Ts |
| 59 | 2 | 2 | $n\text{-}C_4H_9$ | $n\text{-}C_4H_9$ | Ts |
| 60 | 2 | 2 | $n\text{-}C_4H_9$ | $n\text{-}C_4H_9$ | Pic |
| 61 | 2 | 2 | $CH_3$ | $(CH_2)_3$-C₆H₄-$OCH_3$ | Ts |
| 62 | 2 | 2 | $CH_3$ | $(CH_2)_3$-C₆H₄-$OCH_3$ | Pic |
| 63 | 2 | 3 | $CH_3$ | $CH_3$ | Ts |
| 64 | 1 | 4 | $CH_3$ | $CH_3$ | Ts |
| 65 | 1 | 4 | $CH_3$ | $CH_3$ | I |
| 66 | 1 | 4 | $CH_3$ | $CH_3$ | $CH_3COO$ |
| 67 | 1 | 4 | $CH_3$ | $CH_3$ | $CH_3CH(OH)COO$ |
| 68 | 1 | 4 | $CH_3$ | $n\text{-}C_4H_9$ | Ts |
| 69 | 1 | 4 | $CH_3$ | $n\text{-}C_4H_9$ | Pic |
| 70 | 1 | 4 | $n\text{-}C_4H_9$ | $sec\text{-}C_4H_9$ | Cl |
| 71 | 1 | 4 | $n\text{-}C_4H_9$ | $sec\text{-}C_4H_9$ | Ts |
| 72 | 1 | 4 | $C_2H_5$ | $n\text{-}C_{10}H_{21}$ | Ts |
| 73 | 1 | 4 | $CH_3$ | $C_2H_4OCO$-C₆H₅ | Ts |
| 74 | 1 | 5 | $CH_3$ | $C_2H_5$ | Ts |

TABLE 1-continued $$\text{(I)} \quad \underset{(CH_2)_n}{\overset{O}{\diagdown}}\!\!\!\!\!\!\!\!\!\diagup\!\!-(CH_2)_m S^{\oplus}\!\!\!\overset{R_1}{\underset{R_2}{\diagdown}}\; Y_1^{\ominus}$$

| Comp. No. | n | m | R₁ | R₂ | Y₁ |
|---|---|---|---|---|---|
| 75 | 1 | 5 | CH₃ | C₂H₅ | cyclohexyl-NHSO₃ |
| 76 | 1 | 5 | C₂H₅ | CH₂-C₆H₅ (benzyl) | Ts |
| 77 | 1 | 5 | n-C₃H₇ | n-C₆H₁₃ | Ts |
| 78 | 1 | 5 | n-C₃H₇ | n-C₆H₁₃ | I |
| 79 | 1 | 5 | n-C₃H₇ | n-C₆H₁₃ | ClO₄ |
| 80 | 1 | 5 | CH₂-C₆H₅ (benzyl) | CH₂-C₆H₅ (benzyl) | Ts |
| 81 | 1 | 5 | CH₂-C₆H₅ (benzyl) | CH₂-C₆H₅ (benzyl) | Br |
| 82 | 1 | 6 | CH₃ | CH₃ | Cl |
| 83 | 1 | 6 | CH₃ | CH₃ | Ts |
| 84 | 1 | 6 | C₂H₅ | C₂H₅ | I |
| 85 | 1 | 6 | C₂H₅ | C₂H₅ | nicotinate (pyridine-3-COO) |
| 86 | 1 | 6 | cyclopentyl | n-C₃H₇ | Ts |
| 87 | 1 | 5 | CH₃ | C₂H₅ | Br |
| 88 | 1 | 4 | CH₃ | C₂H₄-(tetrahydrofuran-2-yl) | H₂PO₄ |
| 89 | 1 | 7 | n-C₄H₉ | n-C₆H₁₃ | Ts |
| 90 | 1 | 8 | CH₃ | CH₃ | Cl |
| 91 | 1 | 9 | CH₃ | CH₃ | I |
| 92 | 1 | 9 | CH₃ | n-C₄H₉ | Ts |
| 93 | 1 | 10 | C₂H₅ | C₆H₅ (phenyl) | Ts |
| 94 | 1 | 10 | CH₃ | CH₂-cyclopropyl | Ts |
| 95 | 1 | 12 | C₂H₅ | 4-Cl-C₆H₄ | Ts |

TABLE 1-continued

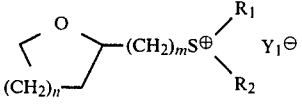
(I)

| Comp. No. | n | m | R₁ | R₂ | Y₁ |
|---|---|---|---|---|---|
| 96 | 1 | 12 | $C_2H_5$ |  | $CH_3\underset{\underset{OH}{\mid}}{C}HCOO$ |
| 97 | 1 | 15 | n-$C_4H_9$ | iso-$C_3H_7$ | Br |
| 98 | 1 | 15 | n-$C_4H_9$ | $CH_2CH=CH_2$ | Ts |
| 99 | 2 | 4 | $CH_3$ | $CH_3$ | $H_2PO_4$ |
| 100 | 2 | 4 | $CH_3$ | $CH_3$ | Ts |
| 101 | 2 | 4 | $CH_3$ | $CH_3$ | I |
| 102 | 2 | 4 | $CH_3$ | $CH_3$ | $\frac{1}{3}\cdot\underset{\underset{CH_2COO}{\mid}}{\underset{\mid}{C}(OH)COO}\atop{CH_2COO}$ |
| 103 | 2 | 4 | $CH_3$ | 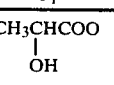 | Ts |
| 104 | 2 | 4 | $CH_3$ | 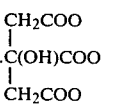 | Pic |
| 105 | 2 | 4 | $C_2H_5$ | n-$C_7H_{15}$ | I |
| 106 | 2 | 4 | sec-$C_4H_9$ | sec-$C_4H_9$ | Ts |
| 107 | 2 | 4 | sec-$C_4H_9$ | sec-$C_4H_9$ | Br |
| 108 | 2 | 5 | $CH_3$ | $CH_3$ | Ts |
| 109 | 2 | 5 | $CH_3$ | $CH_3$ | $\frac{1}{2}\cdot H_2C\underset{COO}{\overset{COO}{<}}$ |
| 110 | 2 | 5 | $CH_3$ | $CH_3$ | I |
| 111 | 2 | 5 | $C_2H_5$ |  | Ts |
| 112 | 2 | 5 | n-$C_3H_7$ | n-$C_4H_9$ | Ts |
| 113 | 2 | 5 | n-$C_3H_7$ | n-$C_4H_9$ | I |
| 114 | 2 | 5 | n-$C_3H_7$ | n-$C_4H_9$ | $\frac{1}{2}\cdot\underset{CHCOO}{\overset{CHCOO}{\|}}$ |
| 115 | 2 | 5 | n-$C_5H_{11}$ | n-$C_8H_{17}$ | Ts |
| 116 | 2 | 6 | $CH_3$ | $CH_3$ | Ts |
| 117 | 2 | 6 | $CH_3$ | $CH_3$ |  |
| 118 | 2 | 6 | n-$C_4H_9$ | 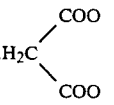 | Ts |

TABLE 1-continued $$\underset{(CH_2)_n}{\overset{O}{\diagdown}}\!\!\!-\!(CH_2)_m S^{\oplus}\!\!\!\underset{R_2}{\overset{R_1}{\diagdown}} \quad Y_1^{\ominus} \quad (I)$$

| Comp. No. | n | m | $R_1$ | $R_2$ | $Y_1$ |
|---|---|---|---|---|---|
| 119 | 2 | 6 | n-$C_4H_9$ | cyclohexyl | nicotinate (pyridine-3-COO) |
| 120 | 2 | 6 | $CH_3$ | phenyl | $CH_3SO_3$ |
| 121 | 2 | 6 | n-$C_4H_9$ | $CH_2$—$CH$=$CH_2$ | Br |
| 122 | 2 | 5 | n-$C_4H_9$ | $C_2H_4$-(tetrahydrofuran-2-yl) | I |
| 123 | 2 | 7 | $CH_3$ | $CH_3$ | Br |
| 124 | 2 | 8 | n-$C_3H_7$ | $CH_2$-phenyl | ½·$\underset{CHCOO}{\overset{CHCOO}{\|}}$ |
| 125 | 2 | 8 | iso-$C_3H_7$ | $CH_2$-cyclopropyl | Ts |
| 126 | 2 | 8 | $CH_3$ | $(CH_2)_3$-(tetrahydropyran-2-yl) | Ts |
| 127 | 2 | 8 | $CH_3$ | 4-$OCH_3$-phenyl | I |
| 128 | 2 | 9 | n-$C_4H_9$ | cyclopentyl | I |
| 129 | 2 | 10 | $CH_3$ | n-$C_8H_{17}$ | Ts |
| 130 | 2 | 11 | n-$C_5H_{11}$ | $C_2H_4$-phenyl | $CH_3COO$ |
| 131 | 2 | 13 | n-$C_3H_7$ | $CH_2$-(tetrahydrofuran-2-yl) | Br |
| 132 | 2 | 14 | $CH_3$ | $CH_3$ | Ts |
| 133 | 2 | 15 | n-$C_4H_9$ | 4-$CH_3$-phenyl | nicotinate (pyridine-3-COO) |

Examples of preferable compounds of this invention other than those given in Table 1 above include halides, inorganic acid salts and organic acid salts of the following sulfonium compounds.

Methylene(tetrahydro-2-furanyl)dipropylsulfonium
Methylene(tetrahydro-2-furanyl)propylpentylsulfonium Methylene(tetrahydro-2-pyranyl)methylphenethylsulfonium
Methylene(tetrahydro-2-pyranyl)ethylpropylsulfonium
Methylene(tetrahydro-2-pyranyl)hexyloctylsulfonium
Ethylene(tetrahydro-2-furanyl)methyloctylsulfonium
Ethylene(tetrahydro-2-furanyl)ethylcyclopentylsulfonium
Ethylene(tetrahydro-2-furanyl)ethylcyclohexylsulfonium
Ethylene(tetrahydro-2-furanyl)dihexylsulfonium
Ethylene(tetrahydro-2-furanyl)dibenzylsulfonium
Ethylene(tetrahydro-2-furanyl)dicyclohexylsulfonium
Ethylene(tetrahydro-2-pyranyl)diethylsulfonium
Ethylene(tetrahydro-2-pyranyl)ethyl-p-chlorophenylsulfonium
Ethylene(tetrahydro-2-pyranyl)dipropylsulfonium
Ethylene(tetrahydro-2-pyranyl)propylphenethylsulfonium
Ethylene(tetrahydro-2-pyranyl)dibutylsulfonium
Ethylene(tetrahydro-2-pyranyl)dihexylsulfonium
Ethylene(tetrahydro-2-pyranyl)dibenzylsulfonium
Ethylene(tetrahydro-2-pyranyl)ethylhexylsulfonium
Propylene(tetrahydro-2-furanyl)dibutylsulfonium
Propylene(tetrahydro-2-furanyl)methylpropylsulfonium
Propylene(tetrahydro-2-furanyl)methylbutylsulfonium
Propylene(tetrahydro-2-furanyl)ethyldecylsulfonium
Propylene(tetrahydro-2-furanyl)butyl-p-methoxyphenylsulfonium
Propylene(tetrahydro-2-furanyl)hexylcyclopentylsulfonium
Propylene(tetrahydro-2-furanyl)hexylcyclohexylsulfonium
Propylene(tetrahydro-2-furanyl)hexylbenzylsulfonium
Propylene(tetrahydro-2-furanyl)dibenzylsulfonium
Propylene(tetrahydro-2-furanyl)diphenethylsulfonium
Propylene(tetrahydro-2-furanyl)diphenylsulfonium
Propylene(tetrahydro-2-furanyl)phenylbenzylsulfonium
Propylene(tetrahydro-2-pyranyl)diethylsulfonium
Propylene(tetrahydro-2-pyranyl)ethylpropylsulfonium
Propylene(tetrahydro-2-pyranyl)ethyloctylsulfonium
Propylene(tetrahydro-2-pyranyl)dipropylsulfonium
Propylene(tetrahydro-2-pyranyl)dibutylsulfonium
Propylene(tetrahydro-2-pyranyl)butylcyclohexylsulfonium
Propylene(tetrahydro-2-pyranyl)didecylsulfonium
Propylene(tetrahydro-2-pyranyl)dicyclopentylsulfonium
Propylene(tetrahydro-2-pyranyl)cyclopentylcyclohexylsulfonium
Propylene(tetrahydro-2-pyranyl)cyclohexylphenethylsulfonium
Propylene(tetrahydro-2-pyranyl)dibenzylsulfonium
Diethyl-4-(tetrahydro-2-furanyl)butylsulfonium
Dibenzyl-4-(tetrahydro-2-furanyl)butylsulfonium
Ethylcyclohexyl-4-(tetrahydro-2-furanyl)butylsulfonium
Hexylphenyl-4-(tetrahydro-2-furanyl)butylsulfonium
Methyl-3-butenyl-4-(tetrahydro-2-furanyl)butylsulfonium
Dibenzyl-4-(tetrahydro-2-pyranyl)butylsulfonium
Dicyclohexyl-4-(tetrahydro-2-pyranyl)butylsulfonium
Hexylallyl-4-(tetrahydro-2-pyranyl)butylsulfonium
Methyl-sec-butyl-5-(tetrahydro-2-furanyl)pentylsulfonium
Dioctyl-5-(tetrahydro-2-furanyl)pentylsulfonium
Benzylphenethyl-5-(tetrahydro-2-furanyl)pentylsulfonium
Dibutyl-5-(tetrahydro-2-pyranyl)pentylsulfonium
Isohexylphenyl-5-(tetrahydro-2-pyranyl)pentylsulfonium
Diphenethyl-5-(tetrahydro-2-pyranyl)pentylsulfonium
Dibenzyl-5-(tetrahydro-2-pyranyl)pentylsulfonium
Ethyl-iso-propyl-6-(tetrahydro-2-furanyl)hexylsulfonium
Methyl(tetrahydro-2-pyranyl)pentyl-6-(tetrahydro-2-furanyl)hexylsulfonium
Dibenzyl-6-(tetrahydro-2-furanyl)herylsulfonium
Methylpropyl-6-(tetrahydro-2-pyranyl)hexylsulfonium
Heptylcyclopropylmethyl-6-(tetrahydro-2-pyranyl)hexylsulfonium
Diphenyl-6-(tetrahydro-2-pyranyl)hexylsulfonium
Benzylphenethyl-6-(tetrahydro-2-pyranyl)hexylsulfonium
Diphenethyl-6-(tetrahydro-2-pyranyl)hexylsulfonium
Dimethyl-7-(tetrahydro-2-furanyl)heptylsulfonium
Propyloctyl-7-(tetrahydro-2-furanyl)heptylsulfonium
Dicyclopentylmethyl-7-(tetrahydro-2-furanyl)heptylsulfonium
Diethyl-7-(tetrahydro-2-pyranyl)heptylsulfonium
Methylpentyl-7-(tetrahydro-2-pyranyl)heptylsulfonium
Phenylbenzyl-7-(tetrahydro-2-pyranyl)heptylsulfonium
Dipropyl-8-(tetrahydro-2-furanyl)octylsulfonium
Di-isopropyl-8-(tetrahydro-2-furanyl)octylsulfonium
Methylnonyl-8-(tetrahydro-2-furanyl)octylsulfonium
Ethyl-isohexyl-8-(tetrahydro-2-pyranyl)octylsulfonium
Dioctyl-8-(tetrahydro-2-pyranyl)octylsulfonium
Butylcyclohexyl-8-(tetrahydro-2-pyranyl)octylsulfonium
Butylcyclopentyl-9-(tetrahydro-2-furanyl)nonylsulfonium
Methylphenethyl-9-(tetrahydro-2-furanyl)nonylsulfonium
Propyl(tetrahydro-2-furanyl)methyl-9-(tetrahydro-2-furanyl)nonylsulfonium
Ethyl-m-chlorobenzyl-9-(tetrahydro-2-furanyl)nonylsulfonium
Methyloctyl-9-(tetrahydro-2-pyranyl)nonylsulfonium
Hexylphenyl-9-(tetrahydro-2-pyranyl)nonylsulfonium
Di(tetrahydro-2-furanyl)methyl-9-(tetrahydro-2-pyranyl)nonylsulfonium
Diethyl-10-(tetrahydro-2-furanyl)decylsulfonium
Ethyl-t-butyl-10-(tetrahydro-2-furanyl)decylsulfonium
Diallyl-10-(tetrahydro-2-furanyl)decylsulfonium
Propyldecyl-10-(tetrahydro-2-pyranyl)decylsulfonium
Diethyl-10-(tetrahydro-2-pyranyl)decylsulfonium
Methylhexyl-10-(tetrahydro-2-pyranyl)decylsulfonium
Octyldecyl-11-(tetrahydro-2-furanyl)undecanylsulfonium
Butylallyl-11-(tetrahydro-2-furanyl)undecanylsulfonium
Ethyl-p-chlorophenyl-11-(tetrahydro-2-furanyl)undecanylsulfonium
Dibutyl-11-(tetrahydro-2-pyranyl)undecanylsulfonium
Ethyldecyl-11-(tetrahydro-2-pyranyl)undecanylsulfonium
Ethylcyclohexyl-11-(tetrahydro-2-pyranyl)undecanylsulfonium
Dibutyl-12-(tetrahydro-2-furanyl)dodecanylsulfonium
Dioctyl-12-(tetrahydro-2-furanyl)dodecanylsulfonium
Cyclopentylcyclohexyl-12-(tetrahydro-2-furanyl)dodecanylsulfonium
Heptyl-(tetrahydro-2-pyranyl)methyl-12-(tetrahydro-2-furanyl)dodecanylsulfonium Ethylbenzyl-12-(tetrahydro-2-pyranyl)dodecanylsulfonium
Butyldecyl-12-(tetrahydro-2-pyranyl)dodecanylsulfonium
Propyl-p-methoxyphenyl-12-(tetrahydro-2-pyranyl)dodecanylsulfonium
Methyl-isopropyl-12-(tetrahydro-2-pyranyl)dodecanylsulfonium
Propylcyclopentyl-13-(tetrahydro-2-furanyl)tridecanylsulfonium
Hexyldecyl-13-(tetrahydro-2-furanyl)tridecanylsulfonium
Dicyclohexyl-13-(tetrahydro-2-furanyl)tridecanylsulfonium
Hexylcyclopentyl-13-(tetrahydro-2-pyranyl)tridecanylsulfonium
Butyl-o-methylphenyl-13-(tetrahydro-2-pyranyl)tridecanylsulfonium
Propylbenzoyloxyethyl-13-(tetrahydro-2-pyranyl)tridecanylsulfonium
Butylbenzoyloxyethyl-13-tetrahydro-2-pyranyl)tridecanylsulfonium
Dibutyl-14-(tetrahydro-2-furanyl)tetradecanylsulfonium
Dinonyl-14-(tetrahydro-2-furanyl)tetradecanylsulfonium
Cyclopentylphenethyl-14-(tetrahydro-2-furanyl)tetradecanylsulfonium
Hexylcyclohexyl-14-(tetrahydro-2-furanyl)tetradecanylsulfonium
Isopentylcyclohexyl-14-(tetrahydro-2-furanyl)tetradecanylsulfonium
Hexylcyclohexyl-14-(tetrahydro-2-pyranyl)tetradecanylsulfonium
Butyl(tetrahydro-2-furanyl)butyl-14-(tetrahydro-2-pyranyl)tetradecanylsulfonium
Dipropyl-14-(tetrahydro-2-pyranyl)tetradecanylsulfonium
Nonyldecyl-15-(tetrahydro-2-furanyl)pentadecanylsulfonium
Butylphenylpropyl-15-(tetrahydro-2-furanyl)pentadecanylsulfonium
Benzylcyclopropylmethyl-15-(tetrahydro-2-furanyl)pentadecanylsulfonium
Hexylbenzyl-15-(tetrahydro-2-pyranyl)pentadecanylsulfonium
Dihexyl-15-(tetrahydro-2-pyranyl)pentadecanylsulfonium
Dimethyl-15-(tetrahydro-2-pyranyl)pentadecanylsulfonium
Dicyclopropylmethyl-15-(tetrahydro-2-pyranyl)pentadecanylsulfonium The sulfonium compounds represented by the formula (I) have immunostimulant activity, anti-inflammatory activity and analgesic activity, act against rheumatism, auto-immunization, allergy and asthma, improve liver function, afford defenses against infections, prevent side effects of compounds, such as steroids and anticancer drugs, which have immunosuppressive activity as a side effect, assist in immunotherapy, inhibit coagulation of platelets and control growth of plants and animals. The present compounds are therefore useful as the active components of drugs and agricultural chemicals.

The compounds of this invention can be prepared, for example, by the process shown by the following reaction equation, in which a sulfide compound of the formula (II) is reacted with a compound of the formula (III).

(Reaction A)

$$\underset{(II)}{\underset{(CH_2)_n}{\overset{O}{\diagup}}\hspace{-2pt}\diagdown\hspace{-4pt}-(CH_2)_mSR_1} + R_2Y_1 \longrightarrow$$

$$\underset{(I)}{\underset{(CH_2)_n}{\overset{O}{\diagup}}\hspace{-2pt}\diagdown\hspace{-4pt}-(CH_2)_mS^{\oplus}\underset{R_2}{\overset{R_1}{\diagdown\hspace{-2pt}\diagup}}\quad Y_1^{\ominus}}$$

wherein $R_1$, $R_2$, $Y_1$, n and m are as defined above.

Useful starting compounds of the formula (II) are sulfide compounds in which $R_1$, n and m are in corresponding relation to those of the compound (I) to be prepared. Examples of such compounds are given below.

Methylene(tetrahydro-2-furanyl)methylsulfide
Methylene(tetrahydro-2-furanyl)propylsulfide
Methylene(tetrahydro-2-furanyl)butylsulfide
Methylene(tetrahydro-2-furanyl)decylsulfide
Methylene(tetrahydro-2-furanyl)cyclopentylsulfide
Methylene(tetrahydro-2-furanyl)phenylsulfide
Methylene(tetrahydro-2-furanyl)benzylsulfide
Methylene(tetrahydro-2-furanyl)phenethylsulfide
Methylene(tetrahydro-2-pyranyl)methylsulfide
Methylene(tetrahydro-2-pyranyl)ethylsulfide
Methylene(tetrahydro-2-pyranyl)cyclohexylsulfide
Methylene(tetrahydro-2-pyranyl)allylsulfide
Methylene(tetrahydro-2-pyranyl)phenylsulfide
Ethylene(tetrahydro-2-furanyl)methylsulfide
Ethylene(tetrahydro-2-furanyl)butylsulfide
Ethylene(tetrahydro-2-furanyl)hexylsulfide
Ethylene(tetrahydro-2-furanyl)phenylsulfide
Ethylene(tetrahydro-2-furanyl)-o-methylphenethylsulfide
Ethylene(tetrahydro-2-pyranyl)methylsulfide
Ethylene(tetrahydro-2-pyranyl)butylsulfide
Ethylene(tetrahydro-2-pyranyl)benzylsulfide
Propylene(tetrahydro-2-furanyl)methylsulfide
Propylene(tetrahydro-2-furanyl)ethylsulfide
Propylene(tetrahydro-2-furanyl)propylsulfide
Propylene(tetrahydro-2-furanyl)decylsulfide
Propylene(tetrahydro-2-furanyl)cyclohexylsulfide
Propylene(tetrahydro-2-furanyl)benzylsulfide
Propylene(tetrahydro-2-pyranyl)methylsulfide
Propylene(tetrahydro-2-pyranyl)ethylsulfide
Propylene(tetrahydro-2-pyranyl)propylsulfide
Propylene(tetrahydro-2-pyranyl)octylsulfide
Propylene(tetrahydro-2-pyranyl)benzylsulfide
Methyl-4-(tetrahydro-2-furanyl)butylsulfide
Nonyl-4-(tetrahydro-2-furanyl)butylsulfide
(Tetrahydro-2-furanyl)pentyl-4-(tetrahydro-2-furanyl)butylsulfide
Butyl-4-(tetrahydro-2-pyranyl)butylsulfide
Cyclohexyl-4-(tetrahydro-2-pyranyl)butylsulfide
Ethyl-5-(tetrahydro-2-furanyl)pentylsulfide
Allyl-5-(tetrahydro-2-furanyl)pentylsulfide
Isopentyl-5-(tetrahydro-2-pyranyl)pentylsulfide
Phenyl-5-(tetrahydro-2-pyranyl)pentylsulfide
Propyl-6-(tetrahydro-2-furanyl)hexylsulfide
Cyclopentyl-6-(tetrahydro-2-furanyl)hexylsulfide
sec-Butyl-6-(tetrahydro-2-pyranyl)hexylsulfide Benzyl-6-(tetrahydro-2-pyranyl)hexylsulfide
Butyl-7-(tetrahydro-2-furanyl)heptylsulfide
Phenyl-7-(tetrahydro-2-furanyl)heptylsulfide
(Tetrahydro-2-pyranyl)propyl-7-(tetrahydro-2-pyranyl)heptylsulfide
Phenethyl-7-(tetrahydro-2-pyranyl)heptylsulfide
Isohexyl-8-(tetrahydro-2-furanyl)octylsulfide
Benzyl-8-(tetrahydro-2-furanyl)octylsulfide
Octyl-8-(tetrahydro-2-pyranyl)octylsulfide
p-Methoxyphenyl-8-(tetrahydro-2-pyranyl)octylsulfide
Decyl-9-(tetrahydro-2-furanyl)nonylsulfide
(Tetrahydro-2-furanyl)ethyl-9-(tetrahydro-2-furanyl)nonylsulfide
Phenylpropyl-9-(tetrahydro-2-pyranyl)nonylsulfide
Cyclohexyl-10-(tetrahydro-2-furanyl)decylsulfide
Ethyl-10-(tetrahydro-2-pyranyl)decylsulfide
(Tetrahydro-2-pyranyl)methyl-10-(tetrahydro-2-pyranyl)decylsulfide
Butyl-11-(tetrahydro-2-furanyl)undecanylsulfide
Benzyl-11-(tetrahydro-2-furanyl)undecanylsulfide
Nonyl-11-(tetrahydro-2-pyranyl)undecanylsulfide
Hexyl-12-(tetrahydro-2-furanyl)dodecanylsulfide
Cyclopropylmethyl-12-(tetrahydro-2-pyranyl)dodecanylsulfide
Phenethyl-12-(tetrahydro-2-pyranyl)dodecanylsulfide
Methyl-13-(tetrahydro-2-furanyl)tridecanylsulfide
Cyclohexyl-13-(tetrahydro-2-furanyl)tridecanylsulfide
Benzoyloxymethyl-13-(tetrahydro-2-pyranyl)tridecanylsulfide
o-Methylphenethyl-14-(tetrahydro-2-furanyl)tetradecanylsulfide
Isopentyl-14-(tetrahydro-2-pyranyl)tetradecanylsulfide
Hexyl-14-(tetrahydro-2-pyranyl)tetradecanylsulfide
Octyl-15-(tetrahydro-2-furanyl)pentadecanylsulfide
Methyl-15-(tetrahydro-2-pyranyl)pentadecanylsulfide
Benzyl-15-(tetrahydro-2-pyranyl)pentadecanylsulfide These sulfide compounds of the formula (II) usable as starting compounds are novel and can be prepared, for example, by the process shown by the following reaction equation, in which a known halide of the formula (IV) is reacted with a known mercaptan of the formula (V).

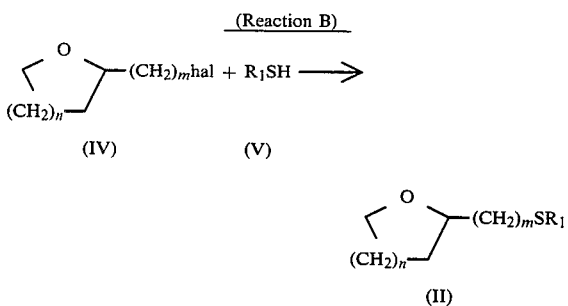

wherein $R_1$, n and m are as defined above, and hal represents halogen.

This reaction can be conducted in a solvent or without using any solvent, usually at about 0° to about 200° C., preferably at room temperature to about 150° C., for about 0.5 to 24 hours, preferably in the presence of a basic compound. Examples of useful basic compounds are alkali metals such as sodium and potassium; alkali metal hydrides such as sodium hydride, potassium hydride and lithium hydride; alkali metal hydroxides such as sodium hydroxide and potassium hydroxide; and like usual basic compounds. Examples of useful solvents are alcohols such as methanol, ethanol and butanol; ethers such as ethyl ether and propyl ether; polar solvents such as acetonitrile, nitromethane and pyridine; halogenated hydrocarbons such as dichloromethane (methylene chloride), dichloroethane (ethylene chloride) and chloroform; aromatic hydrocarbons such as benzene, toluene and xylene; and water. Preferably 1 to 4 moles of the mercaptan of the formula (V) is used per mole of the halide of the formula (IV). Reference Examples given later show in detail the process for preparing sulfide compounds (II) useful as starting materials.

Useful compounds of the formula (III), the other of the two kinds of starting compounds for preparing the compounds of this invention, are known compounds which correspond to the compounds (I) to be prepared with respect to $R_2$ and $Y_1$. Preferred examples of such compounds are methyl chloride, methyl iodide, ethyl bromide, propyl chloride, cyclopropylmethyl iodide, butyl iodide, butyl bromide, hexyl chloride, cyclohexyl iodide, cyclopropylmethyl bromide, cyclohexyl bromide, cyclopentyl iodide, heptyl iodide, nonyl iodide, decyl bromide, allyl bromide, benzyl chloride, benzyl bromide, octyl iodide, methyl methanesulfonate, ethyl methanesulfonate, methyl p-toluenesulfonate, propyl p-toluenesulfonate, butyl p-toluenesulfonate, octyl p-toluenesulfonate, nonyl p-toluenesulfonate, ethyl nicotinate, methyl benzoate and monomethylphosphate.

The reaction for preparing the present compound is carried out in the absence or presence of a solvent, at about −30° to about 150° C., preferably about 0° to about 100° C. for about 0.5 to about 24 hours. It is preferable to use the compound of the formula (III) in an amount of about 1 to about 4 moles per mole of the sulfide compound (II). Examples of useful solvents are methanol, ethanol propanol and like alcohols; acetonitrile, nitromethane, dimethylformamide, dimethylsulfoxide, pyridine and like polar solvents; dichloromethane, dichloroethane, chloroform and like hydrogenated hydrocarbons; benzene, toluene, xylene and like aromatic hydrocarbons; ethyl ether, propyl ether and like ethers; and others including acetone, ethyl acetate, petroleum ether and water.

In this way, the sulfonium compound of the formula (I) can be prepared. The desired product can be isolated from the reaction mixture by a usual separation method, such as extraction, concentration, distillation, recrystallization or column chromatography.

Of the compounds of this invention prepared by the foregoing reaction, those represented by the following formula (I-a) can be converted by salt exchange to other compounds of the invention represented by the following formula (I-b). This process is shown by the following reaction equation.

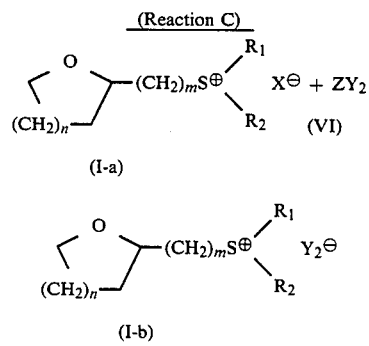

wherein $R_1$, $R_2$, n and m are as defined above, X is a halogen atom, $Y_2$ is a halogen atom different from X or an inorganic acid residue or organic acid residue, and Z is a silver atom or alkali metal.

For this salt exchange reaction, the sulfonium halide of the invention represented by the formula (I-a) may be used as contained in the reaction mixture resulting from the foregoing reaction (Reaction A), or as isolated therefrom.

Useful compounds of the formula (VI) are those capable of giving the groups $Y_2$ of the formula (I-b) and including silver halides or alkali metal halides, and silver salts or alkali metal salts of inorganic acids and organic acids. Examples of suitable halides are chloride, bromide and iodide. Examples of suitable inorganic acids are nitric acid, sulfuric acid, phosphoric acid, metaphosphoric acid and perchloric acid. Examples of suitable organic acids are acetic acid, propionic acid, butyric acid, isobutyric acid, maleic acid, malonic acid, fumaric acid, citric acid, lactic acid, tartaric acid, lauric acid, palmitic acid, stearic acid, linoleic acid, oleic acid, oxalic acid, succinic acid, flavianic acid, camphor-sulfonic acid, ascorbic acid, cyclohexylsulfamic acid, methanesulfonic acid, benzenesulfonic acid, p-toluenesulfonic acid, picrylsulfonic acid, benzoic acid, nicotinic acid, glycyrrhetinic acid, glycyrrhizin, 1,5-naphthalenedisulfonic acid, etc. Examples of alkali metal salts of such inorganic and organic acids are sodium salts, potassium salts and lithium salts.

The reaction can be conducted in a solvent at about $-30°$ to about $150°$ C., preferably about $0°$ to about $100°$ C. for about 0.5 to about 24 hours. The amount of the compound of the formula (VI) to be used based on the sulfonium halide of the formula (I-a) is preferably about 1 to about 4 times the theoretical amount. Any of the solvents already mentioned in the foregoing reaction (Reaction A) is usable for the reaction.

The salt exchange mentioned can be effected also by the following reaction, in which the sulfonium halide of the formula (I-a) is reacted with silver oxide of the following formula (VII) and the resulting sulfonium hydroxide of the following formula (VIII) is reacted with a compound of the following formula (IX) to produce the desired sulfonium compound (I-b).

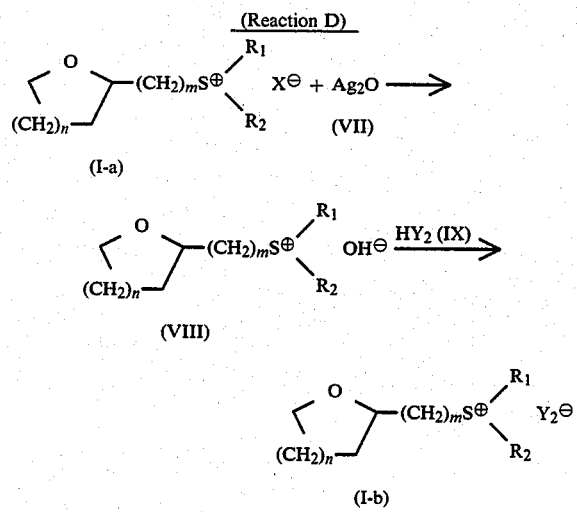

wherein $R_1$, $R_2$, X, $Y_2$, n and m are as defined above.

Examples of useful compounds of the formula (IX) are free organic or inorganic acids already mentioned in the foregoing reaction (Reaction-C). Although the above process can be practiced by placing the sulfonium halide of the formula (I-a), silver oxide (VII) and the compound of the formula (IX) in a suitable container at the same time, it is preferable to use a two-stage method by reacting the sulfonium halide with silver oxide first to obtain the sulfonium hydroxide of the formula (VIII) as an intermidiate and subsequently placing the compound (IX) into the reaction system for further reaction with the intermmidate.

The silver oxide (VII) to be used for preparing the sulfonium hydroxide of the formula (VIII) can be used in an amount usually of at least about one mole, preferably about 1 to about 4 moles, per mole of the sulfonium halide (I-a) serving as the starting material. The compound of the formula (IX) can be used in an amount of at least about one mole, preferably about 1 to about 4 moles, per mole of the sulfonium halide (I-a) used as the starting material. The same solvents as already mentioned in the foregoing reaction (Reaction C) are usable for the reactions. The reaction between the sulfonium halide (I-a) and silver oxide (VII), and the reaction between the sulfonium hydroxide (VIII) obtained from the first reaction as an intermediate and the compound of the formula (IX) may be conducted usually at about $-30°$ to about $150°$ C., preferably at about $0°$ to about $100°$ C., for about 0.5 to about 24 hours, respectively.

After the completion of the salt exchange reaction, the desired compound (I-b) can be isolated by the same separation method as already mentioned in the foregoing reaction (Reaction A).

For use as drugs, the compounds of this invention can be given in the form of any of various preparations, such as oral preparation, injection or rectal suppository, in accordance with the purpose of therapy contemplated. Such preparations can be formulated in the manner already known in the art. For the formulation of solid preparations for oral administration, such as tablets, coated tablets, granules, powders and capsules, excipients, binders, disintegrators, lubricants or glazes, etc. can be added to the compounds of this invention. Such additives are already known in the art and useful examples are exipients such as lactose, white sugar, sodium chloride, glucose solution, starch, calcium carbonate, kaolin, crystalline cellulose and silicic acid; binders such as water, ethanol, propanol, glucose, carboxymethylcellulose, shellac, methylcellulose, potassium phosphate and polyvinylpyrrolidone; disintegrators such as dried starch, sodium alginate, agar powder, sodium hydrogencarbonate, calcium carbonate, sodium lauryl sulfate, glyceryl monostearate, starch and lactose; lubricants or glazes such as purified talc, steraric acid salt, boric acid powder solid polyethylene glycol; etc. When desired, the solid preparations may also contain coloring agents, preservatives, perfumes, flavors, sweetening agents, etc. as well as other drugs. For the formulation of liquid preparations for oral administration, such as solutions, syrups and dry syrups, excipients and if desired flavors, buffers, stabilizers, etc. can be added to the present compound. The resulting preparations are given orally. For the formulation of parenteral solutions, pH adjusting agents, buffers, stabilizers, isotonic agents, local anesthetics, etc. can be added to the present compounds. Such solutions can be given subcutaneously, intramuscularly or intravenously. For the preparation of rectal suppositories, excipients, surfactants, etc. can be added to the present compounds. Such suppositories are administered to the rectum.

The amount of the sulfonium compound to be incorporated into the foregoing preparations varies with the symptoms of the patient or with the type of the preparation. Preferably the amount per administration unit is about 5 to about 1000 mg for oral administration, about 0.5 to about 500 mg for parenteral administration and about 5 to about 1000 mg for intrarectal administration. The dosage per day for an adult, which varies with the symptoms, is preferably about 0.5 to about 5000 mg for usual purposes.

Given below are reference examples for producing starting compounds for the preparation of compounds of the invention, and examples for preparing compounds of the invention. The compound numbers in the examples correspond to those listed in Table 1. The properties and yields of the compounds obtained in Examples are shown in the appended Tables 2 and 3. Of these compounds, those obtained in the form of oils are listed in Table 2, in which the NMR values are those determined in DMSO-$d_6$ using TMS as an internal standard substance. The other compounds (including some of the compounds listed in Table 2) are given in Table 3, in which the mark "—" in the column of m.p. (°C.) indicates that the compound concerned is oily.

TABLE 2

| Comp. No. | NMR (δ ppm) | Yield (%) |
|---|---|---|
| 1 | 3.65(2H 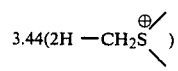) | 94.3 |
| | 4.20(1H 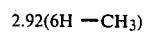) | |
| | 3.44(2H —CH$_2$S$^\oplus$ ) 2.86(6H —CH$_3$) | |
| 3 | 4.20(1H 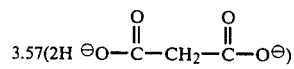) 3.42(2H —CH$_2$S$^\oplus$ ) | 95.6 |
| | 2.86(6H —CH$_3$) | |
| 5 | 3.73(2H 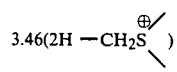) | 95.2 |
| | 3.47(2H —CH$_2$S$^\oplus$ ) | |
| | 2.91(6H —CH$_3$) | |
| 6 | 3.73(2H 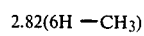) | 94.1 (Ex. 11) |
| | 3.53(2H —CH$_2$S$^\oplus$ ) | |

TABLE 2-continued

| Comp. No. | NMR (δ ppm) | Yield (%) |
|---|---|---|
| | 2.94(6H —S$^\oplus$—CH$_3$) 1.08(3H $^\ominus$OCOCH—CH$_3$) OH | 89.3 (Ex. 15) |
| 7 | 3.74(2H 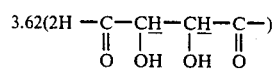) | 93.5 |
| | 3.44(2H —CH$_2$S$^\oplus$ ) | |
| | 2.92(6H —CH$_3$) | |
| | 3.57(2H $^\ominus$O—C(=O)—CH$_2$—C(=O)—O$^\ominus$) | |
| 8 | 3.77(2H 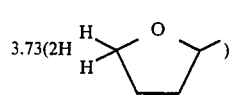) | 94.5 |
| | 3.46(2H —CH$_2$S$^\oplus$ ) | |
| | 2.82(6H —CH$_3$) | |
| | 3.62(2H —C(=O)—CH(OH)—CH(OH)—C(=O)—) | |
| 9 | 3.73(2H 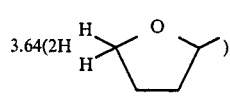) | 95.6 |
| | 3.42(2H —CH$_2$S$^\oplus$ ) | |
| | 2.91(6H —CH$_3$) 6.02(2H —CH=CH—) | |
| 10 | 3.64(2H 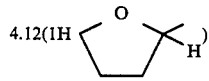) | 90.7 |
| | 4.12(1H 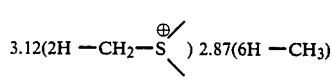) | |
| | 3.12(2H —CH$_2$—S$^\oplus$ ) 2.87(6H —CH$_3$) | |
| 12 | 3.78(2H 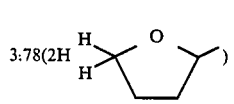) | 93.2 |
| | 4.21(1H ) | |
| | 2.90(3H —S$^\oplus$—CH$_3$) 0.89(3H —(CH$_2$)$_3$CH$_3$) |  |

TABLE 2-continued

| Comp. No. | NMR (δ ppm) | Yield (%) |
|---|---|---|
| 14 | 3.71(2H 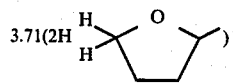) <br> 4.19(1H 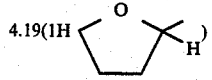) <br> 3.10–3.60(4H CH$_2$—$\overset{\oplus}{S}$—CH$_2$—) <br> 2.89(3H —$\overset{\oplus}{S}$—CH$_3$) <br> 0.80(3H —(CH$_2$)$_9$—C̲H̲$_3$) | 91.6 |
| 16 | 4.19(1H 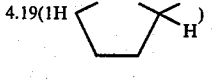) <br> 2.89(3H $\overset{\oplus}{S}$—CH$_3$) <br> 0.80(3H —(CH$_2$)$_9$C̲H̲$_3$) | 96.1 |
| 17 | 3.10–3.90(6H 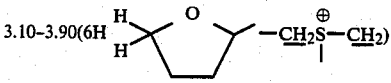) <br> 4.00–4.30(1H 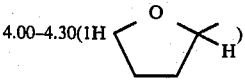) <br> 1.39(6H —CH$\overset{CH_3}{\underset{CH_3}{<}}$) <br> 0.96(3H —CH$_2$CH$_2$C̲H̲$_3$) | 92.5 |
| 18 | 3.30–3.90(6H —C̲H̲$_2$$\overset{\oplus}{S}$$\overset{CH_2—}{\underset{CH_2—}{<}}$) <br> 0.93(3H —(CH$_2$)$_2$C̲H̲$_3$) 0.86(3H —(CH$_2$)$_5$C̲H̲$_3$) | 91.0 |
| 19 | 3.75(2H 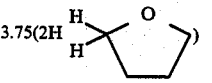) <br> 4.20(1H ) <br> 3.39(2H —CH$_2$$\overset{\oplus}{S}$—) 2.88(3H —CH$_3$) | 90.3 |
| 21 | 3.70(2H 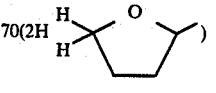) <br> 4.10(1H 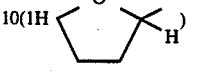) <br> 3.50(2H —CH$_2$—$\overset{\oplus}{S}$—) 3.28(3H —CH$_3$) | 89.3 |
| 23 | 3.65(2H 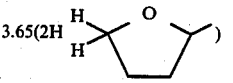) <br> 4.15(1H 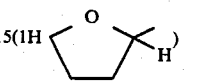) <br> 3.45(2H 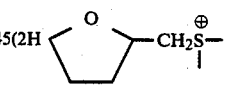) <br> 4.97(2H —$\overset{\oplus}{S}$—C̲H̲$_2$—⟨phenyl⟩) <br> 2.78(3H —CH$_3$) | 89.9 |
| 25 | 3.90(1H ) <br> 3.50(2H —CH$_2$—$\overset{\oplus}{S}$⟨) <br> 4.80(4H —C̲H̲$_2$—⟨phenyl⟩) | 90.1 |
| 27 | 4.22(1H 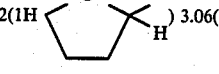) 3.06(3H —CH$_3$) <br> 4.70(2H —$\overset{\oplus}{S}$CH$_2$C̲H̲$_2$OCO—) | 91.5 |
| 30 | 3.64(2H 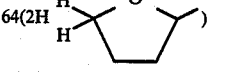) <br> 3.36(2H —CH$_2$—$\overset{\oplus}{S}$⟨) <br> 2.89(6H —CH$_3$) | 93.2 |

TABLE 2-continued

| Comp. No. | NMR (δ ppm) | Yield (%) |
|---|---|---|
| 32 | 3.64(2H, tetrahydrofuran ring CH₂, H H) 3.37(2H —CH₂—S⊕) 2.89(6H —CH₃) | 95.1 |
| 33 | 3.64(2H, tetrahydrofuran ring) 3.36(2H —CH₂—S⊕) 2.88(6H —CH₃) 1.00(3H ⊖OCOCHCH₃ with OH) | 89.2 |
| 34 | 3.64(2H, tetrahydrofuran ring) 3.37(2H —CH₂S⊕) 2.89(6H —CH₃) 3.47(2H —CH₂COO⊖) | 88.7 |
| 35 | 3.71(2H, tetrahydrofuran ring) 3.30(2H —CH₂S⊕) 6.06(2H —C(=O)—CH=) 2.84(6H —CH₃) | 94.5 |
| 36 | 3.56(2H, tetrahydrofuran ring) 3.31(2H —CH₂S⊕) 2.88(6H —CH₃) | 93.2 |
| 40 | 3.61(2H, tetrahydrofuran ring) 3.60-3.90(1H, tetrahydrofuran ring H) 3.10-3.40(4H —CH₂—S⊕—CH₂—) 2.82(3H S⊕—CH₃) 0.85(3H —(CH₂)₃CH₃) | — |
| 41 | 3.53(2H, tetrahydrofuran ring) 3.40-3.80(1H, tetrahydrofuran ring H) 0.85(3H —(CH₂)₇CH₃) 0.96(3H —(CH₂)₂CH₃) | 93.2 |
| 42 | 3.51(2H, tetrahydrofuran ring) 3.5-3.8(2H tetrahydrofuran ring CH₂—) 0.99(6H —CH₂CH(CH₃)₂) | 92.1 |
| 44 | 3.50-3.90(1H, tetrahydrofuran ring H) 2.79(3H S⊕—CH₃) 1.41(9H —C(CH₃)₃) | 94.5 |
| 45 | 3.40-3.60(2H, tetrahydrofuran ring H H) 3.50-3.80(1H, tetrahydrofuran ring H) 2.79(3H S⊕—CH₃) 2.19(3H tolyl-CH₃) | 88.8 |

| Comp. No. | NMR (δ ppm) | Yield (%) |
|---|---|---|
| 47 | 3.54(2H) [tetrahydrofuran ring with H, H, O]<br>3.20(2H, \S⊕—CH₂—)<br>2.82(6H —CH₃) 8.03(1H) [nicotinate, COO⊖]<br>8.86(1H) [nicotinate isomer, COO⊖, H] | 89.1 |
| 48 | 3.55(2H) [tetrahydrofuran ring with H, H, O]<br>3.24(2H —CH₂—S⊕—CH₂— with C₂H₅ and 3-chlorophenyl)<br>3.30(2H, \S⊕—CH₂CH₃)<br>4.70(2H, \S⊕CH₂— 3-chlorophenyl) | 87.6 |
| 51 | 3.70(2H) [tetrahydropyran ring with H, H, O]<br>3.35(2H, \S⊕CH₂—)<br>2.83(6H —CH₃) 8.02(1H) [nicotinate, COO⊖]<br>8.84(1H) [nicotinate isomer, COO⊖, H] | 92.5 |
| 52 | 3.77(2H) [tetrahydropyran ring with H, H, O]<br>3.43(2H, \S⊕—CH₂— tetrahydropyran)<br>3.35(4H, \S⊕CH₂CH₃) | 93.8 |
| 54 | 3.70(2H) [tetrahydropyran ring with H, H, O]<br>3.44(2H —CH₂S⊕CH₂CH₃ with cyclohexyl)<br>1.40(3H —CH₂CH₃) | 93.1 |
| 56 | 3.80(2H) [tetrahydropyran ring with H, H, O]<br>3.45(2H —CH₂S⊕ with CH₂CH= and CH₂CH₃)<br>3.32(2H —CH₂S⊕ with CH₂CH= and CH₂CH₃)<br>1.23(3H —CH₂CH₃) | 86.5 |
| 59 | 3.36(2H —CH₂CH₂S⊕ with two C₄H₉)<br>2.20(4H —CH₂—S⊕ with two CH₂CH₂CH₂CH₃)<br>0.89(6H —S⊕ with two (CH₂)₃CH₃) | 85.2 |
| 61 | 3.72(2H) [tetrahydropyran ring with H, H, O] | 89.3 |

| Comp. No. | NMR (δ ppm) | Yield (%) |
|---|---|---|
|  | 3.20(4H CH₃-S⁺(CH₂-)(CH₂-)) |  |
|  | 3.62(3H C₆H₄-OCH₃) |  |
| 65 | 2.91(6H -S⁺(CH₃)₂) 3.1-3.4(2H >S⁺-CH₂-), 3.4-3.8(3H tetrahydrofuran) | 93.2 |
| 66 | 2.92(6H -S⁺(CH₃)₂) | 85.5 |
|  | 3.2-4.0(5H >S⁺-CH₂-, tetrahydrofuran) |  |
| 67 | 2.85(6H -S⁺(CH₃)₂) | 90.0 |
|  | 3.2-4.0(6H >S⁺-CH₂-, CH₃CH(OH)-COO⁻), tetrahydrofuran |  |
| 68 | 1.03(3H CH₃(CH₂)₃-) 2.88(3H >S⁺CH₃) | 91.5 |
|  | 3.1-4.7(7H -CH₂S⁺-CH₂-, tetrahydrofuran) |  |
| 70 | 0.8-1.1(6H -S⁺((CH₂)₃CH₃)(CHCH₂CH₃)(CH₃)) | 88.8 |
|  | 3.1-3.9(8H, -CH₂-S⁺-CH₂-, CH(CH₃), tetrahydrofuran) |  |

| Comp. No. | NMR (δ ppm) | Yield (%) |
|---|---|---|
| 71 | 0.8-1.1(6H CH₃CH₂CH(CH₃)S⁺-(CH₂)₃CH₃) | 92.3 |
|  | 3.1-3.8(8H -CH-S⁺-CH₂-, CH₂-), tetrahydrofuran |  |
| 72 | 0.86(3H CH₃(CH₂)₉S⁺-) | 93.1 |
|  | 3.1-4.0(9H -CH₂S⁺-CH₂-, CH₂-), tetrahydrofuran |  |
| 73 | 3.00(3H CH₃S⁺-) | 84.9 |
|  | 3.2-3.9(7H -S⁺-CH₂-, CH₂-, tetrahydrofuran) |  |
|  | 4.66(2H -CH₂OC(O)C₆H₅) |  |
|  | 7.8-8.0(2H -OC(O)C₆H₄-) |  |
| 74 | 2.83(3H CH₃-S⁺-) | 92.1 |
|  | 3.40-3.80(3H tetrahydrofuran) |  |
|  | 3.22(2H -S⁺-CH₂(CH₂)₄-, CH₂-) |  |
|  | 3.27(2H CH₃CH₂S⁺-) |  |
| 75 | 2.84(3H >S⁺CH₃) 3.27(2H >S⁺CH₂CH₃) | 90.8 |

TABLE 2-continued

| Comp. No. | NMR (δ ppm) | Yield (%) |
|---|---|---|
| | 3.72(2H, $\overset{\oplus}{S}\underline{CH_2}(CH_2)_4-$) | |
| | 3.40–3.80(3H, tetrahydrofuran ring) | |
| 76 | 3.15–3.80(2H CH$_3$CH$_2$$\overset{\oplus}{S}\underline{CH_2}(CH_2)_4-$) | 90.0 |
| | 5.0(2H, $\underline{CH_2}$–Ph) | |
| | 3.40–3.80(3H, tetrahydrofuran ring) | |
| | 3.45(2H, $\overset{\oplus}{S}\underline{CH_2}CH_3$) | |
| 77 | 3.55–3.95(3H, tetrahydrofuran ring) | 93.3 |
| | 3.28(6H, $-CH_2-\overset{\oplus}{S}-CH_2-$ with $CH_2-$) | |
| 79 | 3.10–3.45(6H $-CH_2-\overset{\oplus}{S}-CH_2-$ with $CH_2-$) | 90.1 |
| | 3.40–3.80(3H, tetrahydrofuran ring) | |
| 80 | 3.22(2H $-\overset{\oplus}{S}-\underline{CH_2}(CH_2)_4-$) | 81.7 |
| | 4.78(4H $-\underline{CH_2}-$Ph) | |
| | 7.35–7.65(10H, Ph) | |
| | 3.40–3.80(3H, tetrahydrofuran ring) | |
| 81 | 3.21(2H $-\overset{\oplus}{S}-\underline{CH_2}(CH_2)_4-$) | 90.3 |
| | 7.35–7.65(10H, Ph) | |
| | 3.40–3.80(3H, tetrahydrofuran ring) | |
| | 4.77(4H $-\underline{CH_2}-$Ph) | |
| 82 | 2.89(6H $-\overset{\oplus}{S}(CH_3)_2$) | 90.9 |
| | 3.0–3.9(5H $\overset{\oplus}{S}\underline{CH_2}(CH_2)_5-$, tetrahydrofuran ring) | |
| 83 | 2.86(6H $-\overset{\oplus}{S}(CH_3)_2$) | 91.3 |
| | 3.0–3.9(5H $\overset{\oplus}{S}\underline{CH_2}(CH_2)_5-$, tetrahydrofuran ring) | |
| 84 | 1.33(6H ($\underline{CH_3}CH_2)_2S-$) | 93.4 |
| | 3.0–3.9(5H $\overset{\oplus}{S}-\underline{CH_2}(CH_2)_5-$, tetrahydrofuran ring) | |
| | 3.28(4H (CH$_3$$\underline{CH_2})_2\overset{\oplus}{S}-$) | |
| 85 | 1.33(6H ($\underline{CH_3}-CH_2)_2\overset{\oplus}{S}-$) | 76.3 |
| | 3.29(4H (CH$_3$$\underline{CH_2})_2\overset{\oplus}{S}-$) | |
| | 3.0–3.9(5H tetrahydrofuran ring, (CH$_2)_5-\underline{CH_2}-$) | |
| 86 | 1.00(3H $\underline{CH_3}(CH_2)_2\overset{\oplus}{S}$ ) | 90.3 |

TABLE 2-continued

| Comp. No. | NMR (δ ppm) | Yield (%) |
|---|---|---|
| 87 | 3.1–4.0(8H —C̲H₂—S⊕—C̲H₂— cyclopentyl H), tetrahydrofuran ring (H O H) | 92.3 |
| | 2.83(3H \⊕SCH₃/) 3.21(2H —(CH₂)₄C̲H₂S—⊕) | |
| | 3.26(2H CH₃C̲H₂S⊕) | |
| | 3.40–3.80(3H H—O—H tetrahydrofuran) | |
| 88 | 2.87(3H CH₃—S⊕) | 80.9 |
| | 3.0–4.0(10H —C̲H₂CH₂— O ring H H') | |
| | —C̲H₂(CH₂)₃— O ring H H | |
| | 5.01(2H H₂PO₄⁻) | |
| 89 | 3.15–3.40(2H —(CH₂)₆C̲H₂S⊕—) | 80.3 |
| | 3.27(4H —S⊕C̲H₂(CH₂)₂CH₃ \|C̲H₂(CH₂)₄CH₃) | |
| | 3.40–3.80(3H H—O—H) | |
| 90 | 2.86(6H —S⊕(CH₃)₂) | 92.3 |
| | 3.05–3.35(2H —C̲H₂—S⊕) | |
| | 3.40–3.80(3H H—O—H) | |
| 91 | 2.96(6H —S⊕(CH₃)₂) | 90.0 |
| | 3.05–3.35(2H —C̲H₂—S⊕) | |

TABLE 2-continued

| Comp. No. | NMR (δ ppm) | Yield (%) |
|---|---|---|
| | 3.40–3.80(3H H—O—H) | |
| 92 | 2.87(3H \⊕SCH₃/) | 83.9 |
| | 3.02–3.37(2H —(CH₂)₈C̲H₂S⊕/) | |
| | 3.27(2H \⊕S—CH₂(CH₂)₂CH₃/) | |
| | 3.40–3.80(3H H—O—H) | |
| 93 | 3.15–3.40(2H —(CH₂)₉C̲H₂S⊕/) | 91.2 |
| | 3.23(2H \⊕SC̲H₂CH₃/) | |
| | 3.40–3.80(3H H—O—H) | |
| | 8.12(2H phenyl H) | |
| 94 | 0.4–0.8(4H cyclopropyl H) 1.14(1H cyclopropyl H) | 90.3 |
| | 2.85(3H \⊕SCH₃/) | |
| | 3.15–3.40(2H —(CH₂)₉C̲H₂S⊕/) | |
| | 3.40–3.80(3H H—O—H) | |
| 95 | 3.02–3.38(2H —(CH₂)₁₁C̲H₂S⊕/) | 88.9 |

TABLE 2-continued

| Comp. No. | NMR (δ ppm) | Yield (%) |
|---|---|---|
|  | 3.23(2H, \S⊕CH₂CH₃/) |  |
|  | 3.4–3.8(3H, tetrahydrofuran ring H's) |  |
|  | 7.8–8.2(4H, —C₆H₄—Cl) |  |
| 96 | 3.0–3.9(6H, —(CH₂)₁₁CH₂S⊕/\), tetrahydrofuran-cyclohexyl H's, 3.26(2H, \S⊕CH₂CH₃/) | 87.3 |
| 97 | 3.05–3.35(2H, —(CH₂)₁₄CH₂S⊕/\), 3.27(2H, \S⊕CH₂(CH₂)₂CH₃/), 3.60(1H, —CH(CH₃)₂), 3.40–3.80(3H, tetrahydrofuran ring H's) | 88.7 |
| 98 | 0.92(3H, —CH₃), 5.0–6.4(5H, —CH₂—CH=CH₂), 3.05–3.35(2H, —(CH₂)₁₄CH₂S⊕/\), 3.26(2H, \SCH₂(CH₂)₂CH₃/), 3.30–3.70(3H, tetrahydrofuran ring H's) | 90.2 |
| 99 | 2.88(6H, —S⊕(CH₃)₂), 3.20(2H, tetrahydropyran ring H's) | 85.3 |

TABLE 2-continued

| Comp. No. | NMR (δ ppm) | Yield (%) |
|---|---|---|
|  | 3.23(2H, \S⊕—CH₂—/), 3.78(1H, tetrahydropyran ring H) |  |
| 101 | 2.96(6H, —S⊕(CH₃)₂), 3.24(4H, \S⊕CH₂(CH₂)₃—/), tetrahydropyran ring H, 3.80(1H, tetrahydropyran ring H) | 87.9 |
| 102 | 2.88(6H, —S⊕(CH₃)₂), 3.28(4H, \S⊕CH₂—/), tetrahydropyran ring H, 3.78(1H, tetrahydropyran ring H) | 91.1 |
| 103 | 3.10(2H, tetrahydropyran ring H), 3.32(3H, CH₃—S⊕—), 3.60(2H, \S⊕CH₂(CH₂)₃—/), 3.78(1H, tetrahydropyran ring H), 7.78(3H, C₆H₃) | 92.1 |

TABLE 2-continued

| Comp. No. | NMR (δ ppm) | Yield (%) |
|---|---|---|
| | 8.12(2H, phenyl H) | |
| 104 | 3.10(2H, tetrahydropyran H)<br>3.32(3H CH$_3$—S$^\oplus$—)<br>3.60(2H S$^\oplus$CH$_2$(CH$_2$)$_3$—)<br>3.78(1H, tetrahydropyran H)<br>7.78(3H, phenyl H)<br>8.07(2H, phenyl H) | 91.3 |
| 105 | 1.33(3H S$^\oplus$CH$_2$CH$_3$)<br>1.87(3H S(CH$_2$)$_6$CH$_3$)<br>3.27(8H —CH$_2$S$^\oplus$CH$_2$—, CH$_2$—)<br>3.80(1H, tetrahydropyran H) | 91.3 |
| 106 | 3.20(4H S$^\oplus$CH$_2$—, tetrahydropyran H) | 90.2 |
| | 3.60(1H S—CHC$_2$H$_5$, CH$_3$)<br>3.78(1H, tetrahydropyran H) | |
| 107 | 3.22(2H, tetrahydropyran H)<br>3.24(2H S$^\oplus$CH$_2$(CH$_2$)$_3$—)<br>3.70(2H —S(CHCH$_2$CH$_3$)$_2$, CH$_3$)<br>3.8(1H, tetrahydropyran H) | 86.5 |
| 109 | 2.84(6H —S(CH$_3$)$_2$)<br>3.20(2H, tetrahydropyran H)<br>3.28(2H S—CH$_2$(CH$_2$)$_4$—)<br>3.80 (1H, tetrahydropyran H) | 90.0 |
| 110 | 1.92(6H(CH$_3$)$_2$S$^\oplus$—)<br>3.24(4H S$^\oplus$CH$_2$(CH$_2$)$_4$—, tetrahydropyran H)<br>3.80(1H, tetrahydropyran H) | 94.1 |
| 111 | 3.20(2H, tetrahydropyran H)<br>3.23(4H —(CH$_2$)$_4$CH$_2$—S$^\oplus$—CH$_2$CH$_3$) | 89.2 |

| Comp. No. | NMR (δ ppm) | Yield (%) |
|---|---|---|
| | 3.78(1H, tetrahydropyran-H) | |
| | 5.0(2H, -CH₂-C₆H₄-Cl) | |
| 112 | 0.9–1.1(6H CH₃(CH₂)₃-S⁺-(CH₂)₂CH₃), 3.27(8H -CH₂S⁺-CH₂-, CH₂-), 3.78(1H, tetrahydropyran-H) | 91.7 |
| 113 | 3.10–3.30(4H -SCH₂C₃H₇, CH₂C₂H₅), 3.24(4H \N⁺/SCH₂(CH₂)₄-, tetrahydropyran-H), 3.80(1H, tetrahydropyran-H) | 90.5 |
| 114 | 3.20(2H tetrahydropyran-H), 3.10–3.30(4H CH₃CH₂CH₂S⁺-, C₃H₇CH₂), 3.22(2H \N⁺/S-CH₂(CH₂)₄), 3.78(1H, tetrahydropyran-H) | 92.4 |
| 115 | 1.87(6H CH₃(CH₂)₇S⁺(CH₂)₄CH₃) | 87.5 |

| Comp. No. | NMR (δ ppm) | Yield (%) |
|---|---|---|
| | 3.25(8H -CH₂SCH₂-, CH₂-, tetrahydropyran-H), 3.78(1H, tetrahydropyran-H) | |
| 117 | 2.85(6H -S⁺(CH₃)₂) | 93.5 |
| | 3.20(4H \N⁺/SCH₂(CH₂)₅-, tetrahydropyran-H) 3.78(1H, tetrahydropyran-H) | |
| 118 | 1.92(3H CH₃(CH₂)₃-S⁺/) | 92.7 |
| | 3.20(2H tetrahydropyran-H), 3.25(4H -CH₂S⁺-CH₂-), 3.78(1H, tetrahydropyran-H) | |
| 119 | 3.21(2H tetrahydropyran-H), 3.26(4H -(CH₂)₅CH₂S⁺-, C₃H₇CH₂), 3.78(1H, tetrahydropyran-H) | 89.9 |
| 120 | 3.10(2H tetrahydropyran-H) 3.32(3H \S⁺CH₃/), 3.60(2H \N⁺/SCH₂(CH₂)₅-) | 92.5 |

TABLE 2-continued

| Comp. No. | NMR (δ ppm) | Yield (%) |
|---|---|---|
| | 3.78(1H, tetrahydropyran-H) | |
| 121 | 1.92(3H, >S⊕(CH₂)₃CH₃) | 90.8 |
| | 3.80(1H, tetrahydropyran-H) | |
| | 3.22(6H, −S⊕−CH₂(CH₂)₅−, CH₂C₃H₇) | |
| | 3.20(2H, tetrahydropyran, O−CH(H)) | |
| 122 | 0.91(3H, >S⊕(CH₂)₃CH₃) | 93.5 |
| | 3.2−3.9(12H, tetrahydropyran-H, −CH₂S⊕−CH₂−, CH₂) | |
| 123 | 2.92(6H, −S⊕(CH₃)₂) | 92.2 |
| | 3.24(4H, −(CH₂)₆CH₂S⊕, tetrahydropyran-H) | |
| | 3.80(1H, tetrahydropyran-H) | |
| 124 | 1.00(3H, −(CH₂)₂CH₃) | 90.0 |
| | 4.78(2H, −CH₂−Ph) | |
| | 3.20(2H, tetrahydropyran-H) | |
| | 3.22(2H, −(CH₂)₇CH₂S⊕) | |
| | 3.27(2H, >S⊕−CH₂CH₂CH₃) | |
| | 3.78(1H, tetrahydropyran-H) | |
| 125 | 0.4−0.8(4H, cyclopropyl-H) 1.14(1H, cyclopropyl-H) | 87.6 |
| | 3.20(4H, −(CH₂)₇CH₂S⊕, tetrahydropyran-H) | |
| | 3.30(2H, −CH₂-cyclopropyl) | |
| | 3.60(1H, −CH(CH₃)₂) | |
| | 3.78(1H, tetrahydropyran-H) | |
| 126 | 2.84(3H, >S⊕CH₃) | 90.5 |
| | 3.22(2H, >S⊕CH₂(CH₂)₂-tetrahydropyran) | |
| | 3.24(6H, −(CH₂)₇CH₂S⊕, tetrahydropyran-H) | |
| | 3.80(2H, tetrahydropyran-H) | |
| 127 | 3.14(3H, −S⊕−CH₃) 3.78(1H, tetrahydropyran-H) | 85.6 |
| | 3.21(2H, tetrahydropyran-H) | |

TABLE 2-continued

| Comp. No. | NMR (δ ppm) | Yield (%) |
|---|---|---|
| 128 | 7.13–7.90(4H —C₆H₄—) <br> 3.26(2H —(CH₂)₇—CH₂S⊕(CH₃)₂) <br> 3.76(3H —OCH₃) <br> 1.0(3H (CH₃)₂S⊕—(CH₂)₃CH₃) | 87.5 |
| 129 | 3.2–3.6(7H —CH₂S-cyclopentyl-CH₂—) <br> (tetrahydropyran CH signals ~O-CH-H) <br> 0.87(3H (CH₃)₂S⊕(CH₂)₇CH₃) 2.84(3H (CH₃)₂S⊕CH₃) | 83.3 |
| 130 | 3.25(6H —CH₂S⊕(CH₃)—CH₂—), (tetrahydropyran H) <br> 3.78(1H O-CH-H tetrahydropyran) <br> 1.0(3H (CH₃)₂S⊕(CH₂)₄CH₃) <br> 3.50(2H —CH₂CH₂—C₆H₅) <br> 3.20(2H tetrahydropyran H) <br> 3.60(2H —CH₂CH₂—C₆H₅) <br> 3.22(2H —(CH₂)₁₀CH₂S⊕(CH₃)₂) | 89.6 |
| 131 | 3.78(1H O-CH-H tetrahydropyran) <br> 3.27(2H (CH₃)₂S⊕CH₂(CH₂)₃CH₃) <br> 1.00(3H (CH₃)₂S⊕(CH₂)₂CH₃) <br> 3.80(1H O-CH-H tetrahydropyran) <br> 3.24(4H —(CH₂)₁₂CH₂S⊕(CH₃)₂), (tetrahydropyran H) <br> 3.27(2H (CH₃)₂S⊕CH₂C₂H₅) <br> 3.34(2H (CH₃)₂S⊕CH₂-tetrahydrofuran) <br> 3.65(2H tetrahydrofuran H) | 85.9 |
| 132 | 2.85(6H (CH₃)₂S⊕(CH₃)₂) <br> 3.20(4H —CH₂S⊕(CH₃)₂, tetrahydropyran H) <br> 3.78(1H O-CH-H tetrahydropyran) | 82.4 |
| 133 | 0.92(3H (CH₃)₂S⊕(CH₂)₃CH₃) <br> 3.78(1H O-CH-H tetrahydropyran) | 80.1 |

TABLE 2-continued
| Comp. No. | NMR (δ ppm) | Yield (%) |
|---|---|---|
|  | 2.35(3H— tolyl CH₃); 7.6-8.0(4H— aromatic)  |  |
| 5 | 3.21(2H— tetrahydropyran H); 3.26(4H —CH₂S⁺—CH₂—) 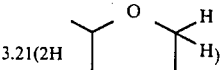 |  |
TABLE 3
| Comp. No. | Elemental analysis | Calc. (%) | Found (%) | Mp. (°C.) | Yield (%) |
|---|---|---|---|---|---|
| 2 | $C_{13}H_{17}N_3O_{10}S_2$ | | | 205–206 | 95.0 |
|  | C | 35.53 | 35.46 | | |
|  | H | 3.90 | 3.94 | | |
|  | N | 9.56 | 9.45 | | |
| 4 | $C_{13}H_{27}NO_4S_2 \cdot (9/10)H_2O$ | | | 63–64 | 90.5 |
|  | C | 45.70 | 45.69 | | |
|  | H | 8.50 | 8.78 | | |
|  | N | 4.10 | 4.29 | | |
| 11 | $C_{49}H_{76}O_{17}S$ | | | 204–205 | 87.0 |
|  | C | 60.72 | 60.77 | | |
|  | H | 7.90 | 7.81 | | |
| 13 | $C_{16}H_{23}N_3O_{10}S_2$ | | | 107–108 | 95.0 |
|  | C | 39.91 | 39.85 | | |
|  | H | 4.81 | 4.88 | | |
|  | N | 8.73 | 8.71 | | |
| 15 | $C_{22}H_{35}N_3O_{10}S_2$ | | | 118.5–119.5 | 93.2 |
|  | C | 46.71 | 46.42 | | |
|  | H | 6.24 | 6.32 | | |
|  | N | 7.43 | 7.63 | | |
| 20 | $C_{17}H_{23}N_3O_{10}S_2$ | | | 111–112 | 89.9 |
|  | C | 41.37 | 41.60 | | |
|  | H | 4.70 | 4.59 | | |
|  | N | 8.51 | 8.31 | | |
| 22 | $C_{18}H_{19}N_3O_{10}S_2$ | | | 171–172 | 92.1 |
|  | C | 43.11 | 42.98 | | |
|  | H | 3.82 | 3.60 | | |
|  | N | 8.38 | 8.09 | | |
| 24 | $C_{19}H_{21}N_3O_{10}S_2$ | | | 129–130 | 91.3 |
|  | C | 44.27 | 44.34 | | |
|  | H | 4.11 | 3.96 | | |
|  | N | 8.15 | 7.91 | | |
| 26 | $C_{25}H_{25}N_3O_{10}S_2$ | | | 148–149 | 92.5 |
|  | C | 50.76 | 50.88 | | |
|  | H | 4.26 | 4.10 | | |
|  | N | 7.10 | 6.98 | | |
| 28 | $C_{21}H_{23}N_3O_{12}S_2$ | | | 180–182 | 90.5 |
|  | C | 43.98 | 44.02 | | |
|  | H | 4.04 | 3.96 | | |
|  | N | 7.33 | 7.22 | | |
| 29 | $C_{15}H_{24}O_4S_2$ | | | 131.5–132 | 94.9 |
|  | C | 54.19 | 54.25 | | |
|  | H | 7.28 | 7.54 | | |
| 31 | $C_8H_{17}OSI$ | | | 87.5–88 | 95.0 |
|  | C | 33.34 | 33.62 | | |
|  | H | 5.95 | 5.93 | | |
| 37 | $C_{14}H_{29}NO_4S_2 \cdot (7/6)H_2O$ | | | 69–70 | 92.0 |
|  | C | 46.79 | 46.65 | | |
|  | H | 8.75 | 8.86 | | |
|  | N | 3.90 | 4.20 | | |
| 38 | $C_{50}H_{78}O_{17}S$ | | | 202–203 | 89.9 |
|  | C | 61.08 | 61.29 | | |
|  | H | 7.10 | 7.20 | | |
| 39 | $C_{17}H_{25}N_3O_{10}S_2$ | | | 100–101 | 95.6 |
|  | C | 41.21 | 41.12 | | |
|  | H | 5.09 | 5.19 | | |
|  | N | 8.48 | 8.43 | | |
| 43 | $C_{17}H_{25}N_3O_{10}S_2$ | | | 116–117.5 | 96.1 |
|  | C | 41.21 | 41.10 | | |
|  | H | 5.09 | 5.09 | | |
|  | N | 8.48 | 8.42 | | |

TABLE 3-continued

| Comp. No. | Elemental analysis | Calc. (%) | Found (%) | Mp. (°C.) | Yield (%) |
|---|---|---|---|---|---|
| 46 | $C_{16}H_{26}O_4S_2$ | | | 129–130 | 90.1 |
| | C | 55.46 | 55.51 | | |
| | H | 7.56 | 7.80 | | |
| 49 | $C_{22}H_{26}N_3O_{10}S_2Cl$ | | | 116.5–117 | 88.8 |
| | C | 44.63 | 44.69 | | |
| | H | 4.43 | 4.53 | | |
| | N | 7.10 | 7.12 | | |
| 50 | $C_{15}H_{24}O_4S_2$ | | | 97–98 | 93.9 |
| | C | 54.19 | 54.16 | | |
| | H | 7.28 | 7.39 | | |
| 53 | $C_{16}H_{23}N_3O_{10}S_2$ | | | 155–156 | 93.2 |
| | C | 39.91 | 39.66 | | |
| | H | 4.81 | 4.88 | | |
| | N | 8.73 | 9.01 | | |
| 55 | $C_{20}H_{29}N_3O_{10}S_2$ | | | 123–124 | 91.1 |
| | C | 44.85 | 44.64 | | |
| | H | 5.46 | 5.70 | | |
| | N | 7.85 | 8.14 | | |
| 57 | $C_{17}H_{23}N_3O_{10}S_2$ | | | 120–120.5 | 89.3 |
| | C | 40.70 | 40.94 | | |
| | H | 4.62 | 4.72 | | |
| | N | 8.38 | 8.66 | | |
| 58 | $C_{16}H_{26}O_4S_2$ | | | 126.5–127 | 92.1 |
| | C | 55.46 | 55.33 | | |
| | H | 7.56 | 7.88 | | |
| 60 | $C_{21}H_{33}N_3O_{10}S_2$ | | | 95–96 | 93.3 |
| | C | 45.72 | 45.79 | | |
| | H | 6.03 | 6.32 | | |
| | N | 7.62 | 7.41 | | |
| 62 | $C_{24}H_{31}N_3O_{11}S_2$ | | | 100–101 | 86.9 |
| | C | 49.91 | 50.05 | | |
| | H | 4.99 | 4.98 | | |
| | N | 6.72 | 6.61 | | |
| 63 | $C_{17}H_{28}O_4S_2$ | | | 120–121 | 95.0 |
| | C | 56.63 | 56.71 | | |
| | H | 7.83 | 7.96 | | |
| 64 | $C_{17}H_{28}O_4S_2$ | | | 166.5–167.5 | 94.5 |
| | C | 56.63 | 56.60 | | |
| | H | 7.83 | 7.85 | | |
| 69 | $C_{19}H_{29}N_3O_{10}S_2$ | | | 105–105.5 | 90.2 |
| | C | 43.59 | 43.29 | | |
| | H | 5.58 | 5.52 | | |
| | N | 8.03 | 8.14 | | |
| 71 | $C_{23}H_{40}O_4S_2$ | | | — | 92.3 |
| | C | 62.12 | 62.11 | | |
| | H | 9.07 | 9.19 | | |
| 72 | $C_{27}H_{48}O_4S_2$ | | | — | 93.1 |
| | C | 64.76 | 65.01 | | |
| | H | 9.66 | 9.77 | | |
| 73 | $C_{25}H_{34}O_6S_2$ | | | — | 84.9 |
| | C | 60.70 | 60.89 | | |
| | H | 6.93 | 6.90 | | |
| 76 | $C_{25}H_{36}O_4S_2$ | | | — | 90.0 |
| | C | 64.62 | 64.88 | | |
| | H | 7.81 | 7.79 | | |
| 78 | $C_{18}H_{37}IOS$ | | | — | 92.5 |
| | C | 50.46 | 50.49 | | |
| | H | 8.70 | 8.88 | | |
| 80 | $C_{30}H_{38}O_4S_2$ | | | — | 81.7 |
| | C | 68.41 | 68.49 | | |
| | H | 7.27 | 7.39 | | |
| 84 | $C_{14}H_{29}IOS$ | | | — | 93.4 |
| | C | 45.16 | 45.08 | | |
| | H | 7.85 | 7.76 | | |
| 85 | $C_{20}H_{33}NO_3S$ | | | — | 76.3 |
| | C | 65.36 | 65.31 | | |
| | H | 9.05 | 9.17 | | |
| | N | 3.81 | 3.69 | | |
| 86 | $C_{25}H_{42}O_4S_2$ | | | — | 90.3 |
| | C | 63.79 | 63.82 | | |
| | H | 8.99 | 9.12 | | |
| 87 | $C_{12}H_{25}BrOS$ | | | — | 92.3 |
| | C | 48.48 | 48.59 | | |
| | H | 8.48 | 8.31 | | |
| 100 | $C_{18}H_{30}O_4S_2$ | | | 166–167 | 93.2 |
| | C | 57.72 | 57.61 | | |
| | H | 8.07 | 8.05 | | |
| 105 | $C_{18}H_{37}IOS$ | | | — | 91.3 |
| | C | 50.46 | 50.42 | | |
| | H | 8.70 | 8.76 | | |

TABLE 3-continued

| Comp. No. | Elemental analysis | Calc. (%) | Found (%) | Mp. (°C.) | Yield (%) |
|---|---|---|---|---|---|
| 106 | $C_{24}H_{42}O_4S_2$ | | | — | 90.2 |
| | C | 62.84 | 62.80 | | |
| | H | 9.23 | 9.20 | | |
| 108 | $C_{19}H_{32}O_4S_2$ | | | 254–255 | 90.5 |
| | C | 58.73 | 58.59 | | |
| | H | 8.30 | 8.55 | | |
| 110 | $C_{12}H_{25}IOS$ | | | — | 94.1 |
| | C | 41.86 | 41.88 | | |
| | H | 7.32 | 7.28 | | |
| 111 | $C_{26}H_{37}ClO_4S_2$ | | | — | 89.2 |
| | C | 60.86 | 60.81 | | |
| | H | 7.27 | 7.30 | | |
| 116 | $C_{20}H_{34}O_4S_2$ | | | 139–140 | 92.1 |
| | C | 59.66 | 59.51 | | |
| | H | 8.51 | 8.66 | | |
| 118 | $C_{28}H_{48}O_4S_2$ | | | — | 92.7 |
| | C | 65.58 | 65.56 | | |
| | H | 9.43 | 9.44 | | |

REFERENCE EXAMPLE 1

A 50 g quantity of methyl mercaptan is added to 100 ml of 18% aqueous solution of sodium hydroxide. With addition of 50 g of methylene(tetrahydro-2-pyranyl)chloride, the mixture is refluxed for 5 hours and cooled. The reaction mixture is extracted with methylene chloride, and the methylene chloride layer is separated, washed with water and dried over anhydrous sodium sulfate. The resulting mixture is then distilled to give 37.5 g (yield 69.1%) of methylene(tetrahydro-2-pyranyl)methyl sulfide, b.p. 69°–70° C./10 mm Hg.

REFERENCE EXAMPLE 2

A 14 g of sodium metal is dissolved in 350 ml of methanol, and 63 g of methyl mercaptan is added to the solution, followed by the addition of 75 g of ethylene(-tetrahydro-2-furanyl)chloride. The mixture is refluxed for 5 hours, cooled and then filtered. The filtrate is distilled to afford 6.6 g (yield 93.7%) of ethylene(tetrahydro-2-furanyl)methyl sulfide, b.p. 113° C./33 mm Hg.

REFERENCE EXAMPLE 3

To 50 ml of methanol are added 0.5 g of sodium metal, 2.8 g of n-octyl mercaptan and 3 g of 5-(tetrahydro-2-pyranyl)-n-pentyl chloride. The mixture is heated at 60°–70° C. for 4 hours. The reaction mixture is distilled to remove the solvent, water and chloroform are added to the residue for extraction, and the chloroform layer is distilled, giving 4.5 g (95.4%) of n-octyl-5-(tetrahydro-2-pyranyl)pentyl sulfide, b.p. 160°–163° C./2–3 mm Hg.

REFERENCE EXAMPLE 4

To 210 ml of 10% aqueous solution of potassium hydroxide are added 25 g of methyl mercaptan and 71 g of 4-(tetrahydro-2-furanyl)butyl bromide. The mixture is stirred at room temperature for 8 hours. The reaction mixture is distilled to remove the solvent and is thereafter treated in the same manner as in Reference Example 3, giving 56.1 g (93.9%) of methyl-4-(tetrahydro-2-furanyl)butyl sulfide, b.p. 101°–102° C./4–5 mm Hg.

EXAMPLE 1

To 70 ml of ether are added 15 g of methylene(tetrahydro-2-pyranyl)methyl sulfide and 38 g of methyl p-toluenesulfonate, and the mixture is stirred at room temperature for 8 hours. The insolubles are filtered off and recrystallized from acetonitrile-ether, giving 32.1 g (yield 93.9%) of methylene(tetrahydro-2-pyranyl)dimethylsulfonium p-toluenesulfonate (Compound 50).

EXAMPLE 2

A 10.2 g quantity of ethylene(tetrahydro-2-furanyl)methyl sulfide and 19 g of methyl p-toluenesulfonate are stirred at room temperature for 6 hours. Ether is added to the reaction mixture, and the insolubles are filtered off and recrystallized from methylene chloride-ether, giving 22.1 g (yield 94.9%) of ethylene(tetrahydro-2-furanyl)dimethylsulfonium p-toluenesulfonate (Compound 29).

EXAMPLE 3

The same method as in Example 2 is repeated with the use of appropriate starting-materials. Compounds 1, 12, 19, 21, 23, 42, 44, 46, 58 and 63 are prepared.

EXAMPLE 4

To a solution of 3.2 g of methylene(tetrahydro-2-pyranyl)ethyl sulfide in 30 ml of methylene chloride are added 6.0 g of ethyl iodide first and 5.6 g of silver p-toluenesulfonate next, and the mixture is stirred at room temperature for 8 hours. The reaction mixture is filtered, the filtrate is further filtered with addition of hydrogen sulfide and active carbon, and the resulting filtrate is concentrated. The concentrate is purified with methylene chloride-ether, giving 6.3 g (yield 93.8%) of methylene(tetrahydro-2-pyranyl)diethylsulfonium p-toluenesulfonate (Compound 52).

EXAMPLE 5

The same method as in Example 4 is repeated with the use of appropriate starting-materials. Compounds 17, 18, 25, 27, 40, 41, 45, 48, 54, 56, 59 and 61 are prepared.

EXAMPLE 6

A 9.5 g quantity of methylene (tetrahydro-2-furanyl)-dimethylsulfonium p-toluenesulfonate is dissolved in water, and 12.6 g of sodium picrylsulfonate is added to the solution. The resulting crystals are recrystallized from ethanol, giving 12.5 g (yield 95%) of methylene(-tetrahydro-2-furanyl)dimethylsulfonium picrylsulfonate (Compound 2).

EXAMPLE 7

The same method as in Example 6 is repeated with the use of appropriate starting-materials. Compounds 13, 15, 20, 22, 24, 26, 28, 39, 43, 49, 53, 55, 57, 60 and 62 are prepared.

EXAMPLE 8

A mixture of 13.2 g of methylene(tetrahydro-2-furanyl)methyl sulfide and 30 g of methyl iodide is stirred at room temperature for 3 hours. Ether is added to the reaction mixture, and the insolubles are filtered off and purified with acetonitrile-ether, giving 26 g (yield 95.6%) of methylene(tetrahydro-2-furanyl)dimethylsulfonium iodide (Compound 3).

EXAMPLE 9

The same method as in Example 8 is repeated with the use of appropriate starting-materials. Compounds 16, 30 and 31 are prepared.

EXAMPLE 10

To 200 ml of ethanol are added 13.7 g of methylene(tetrahydro-2-furanyl)dimethylsulfonium iodide and 15.7 g of silver cyclohexylsulfamate, and the mixture is stirred for 2 hours. The reaction mixture is filtered, and hydrogen sulfide is added to the filtrate, which is then treated with active carbon. The mixture is filtered, the filtrate is concentrated and the concentrate is recrystallized from ethanol-ether, giving 15.4 g (yield 90.5%) of methylene(tetrahydro-2-furanyl)dimethylsulfonium cyclohexyl sulfamate (Compound 4).

EXAMPLE 11

The same method as in Example 10 is repeated with the use of appropriate starting-materials. Compounds 5–10, 32–36, 47 and 51 are prepared.

EXAMPLE 12

To 60 ml of acetonitrile are added 9.8 g of ethylene(tetrahydro-2-furanyl)dimethylsulfonium chloride and 17 g of silver cyclohexylsulfamate, and the mixture is treated at room temperature for 3 hours. The reaction mixture is thereafter treated in the same manner as in Example 10, giving 15.6 g (yield 92%) of ethylene(tetrahydro-2-furanyl)dimethylsulfonium cyclohexyl sulfamate (Compound 37).

EXAMPLE 13

In 150 ml of acetonitrile is dissolved 18.3 g of methylene(tetrahydro-2-furanyl)methyl-n-decylsulfonium iodide, and the solution is stirred at room temperature for 3 hours with addition of 13 g of silver p-toluenesulfonate. The resulting precipitate is filtered off, hydrogen sulfide is added to the filtrate, and the resulting precipitate is filtered off. The filtrate obtained is concentrated, and the concentrate is purified with methylene chloride-ether, affording 18.6 g (yield 91.6%) of methylene(tetrahydro-2-furanyl)methyl-n-decylsulfonium p-toluenesulfonate (Compound 14).

EXAMPLE 14

A 13.7 g quantity of ethylene(tetrahydro-2-furanyl)dimethylsulfonium iodide is dissolved in 400 ml of methanol, 41.2 g of silver oxide is added to the solution, and the mixture is stirred at room temperature for 4 hours and then filtered. A solution of 41.2 g of glycyrrhizin in 300 ml of methanol is added to the filtrate, the mixture is concentrated, and the concentrate is recrystallized from chloroform-ether, giving 42 g (yield 89.9%) of ethylene(tetrahydro-2-furanyl)dimethylsulfonium glycyrrhizate (Compound 38).

EXAMPLE 15

A 26 g quantity of methylene(tetrahydro-2-furanyl)dimethylsulfonium iodide is dissolved in 400 ml of methanol, 23 g of silver oxide is added to the solution, and the mixture is stirred at room temperature for 4 hours and then filtered. A solution of 10 g of lactic acid in 50 ml of methanol is added to the filtrate, the mixture is concentrated, and the concentrate is recrystallized from methanol-ether, giving 20 g (yield 89.3%) of methylene(tetrahydro-2-furanyl)dimethylsulfonium lactate (Compound 6).

EXAMPLE 16

A 13 g quantity of methylene(tetrahydro-2-furanyl)dimethylsulfonium iodide is dissolved in 800 ml of methanol, 41.2 g of silver oxide is added to the solution, and the mixture is stirred at room temperature for 4 hours and then filtered. A solution of 41.2 g of glycyrrhizin in 400 ml of methanol is added to the filtrate, the mixture is concentrated, and the concentrate is recrystallized from chloroform-ether, giving 40 g (yield 87.0%) of methylene(tetrahydro-2-furanyl)dimethylsulfonium glycyrrhizate (Compound 11).

EXAMPLE 17

A 8.7 g quantity of methyl-4-(tetrahydro-2-furanyl)butyl sulfide and 20 g of methyl p-toluenesulfonate are stirred at room temperature for 2 days. Ether is added to the reaction mixture, and the insolubles are filtered off and recrystallized from ethanol-ether, giving 17.0 g (yield 94.5%) of dimethyl-4-(tetrahydro-2-furanyl)butylsulfonium p-toluenesulfonate (Compound 64).

EXAMPLE 18

The same method as in Example 17 is repeated with the use of appropriate starting-materials. Compounds 69, 100 and 116 are prepared.

EXAMPLE 19

A 12.4 g quantity of 2-benzoyloxyethyl-4-(tetrahydro-2-furanyl)butyl sulfide and 2.1 g of methyl p-toluenesulfonate are stirred at room temperature for 3 days. Ether is added to the reaction mixture, and the insolubles are filtered off and recrystallized from methylene chloride-ether, giving 16.9 g (yield 84.9%) of 2-benzoyloxyethylmethyl-4-(tetrahydro-2-furanyl)butylsulfonium p-toluenesulfonate (Compound 73).

EXAMPLE 20

The same method as in Example 19 is repeated with the use of appropriate starting-materials. Compounds 68, 92, 94, 104 and 120 are prepared.

EXAMPLE 21

To 50 ml of ethanol are added 2.64 g of benzyl-5-(tetrahydro-2-furanyl)pentyl sulfide and 40 g of ethyl p-toluenesulfonate, and the mixture is heated at 50°–60° C. for 7 hours. The reaction mixture is distilled to remove the ethanol, and ether is added to the residue, and the insolubles are separated off and purified with methylene chloride-ether, giving 4.2 g (yield 90%) of oily benzylethyl-5-(tetrahydro-2-furanyl)pentylsulfonium p-toluenesulfonate (Compound 76).

EXAMPLE 22

The same method as in Example 21 is repeated with the use of appropriate starting-materials. Compounds 74, 89 and 111 are prepared.

EXAMPLE 23

To 50 ml of dimethylformamide are added 4.32 g of ethyl-6-(tetrahydro-2-furanyl)hexyl sulfide and 4.5 g of ethyl nicotinate, and the mixture is heated at 70°–80° C. for 6 hours. The reaction mixture is distilled to remove the solvent, and ether is added to the residue, and the insolubles are separated off and purified with methylene chloride-ether, giving 5.6 g (yield 76.3%) of oily diethyl-6-(tetrahydro-2-furanyl)hexylsulfonium nicotinate (Compound 85).

EXAMPLE 24

To 10 ml of methylene chloride are added 1.0 g of methyl-5-(tetrahydro-2-pyranyl)pentyl sulfide and 1.5 g of methyl iodide, and the mixture is stirred at room temperature for 7 hours. Ether is added to the reaction mixture, and the insolubles are separated off and purified with methylene chloride-ether, giving 1.6 g (yield 94.1%) of dimethyl-5-(tetrahydro-2-pyranyl)pentylsulfonium iodide (Compound 110).

EXAMPLE 25

The same method as in Example 24 is repeated with the use of appropriate starting-materials. Compounds 65, 70, 78, 81, 82, 84, 87, 90, 91, 97, 101, 105, 107, 113, 121, 122, 123, 127, 128 and 131 are prepared.

EXAMPLE 26

In 100 ml of acetonitrile are added 8.7 g of methyl-4-(tetrahydro-2-furanyl)butyl sulfide, 10.8 g of silver lactate and 14.2 g of methyl iodide, and the mixture is stirred at room temperature for 8 hours. The reaction mixture is filtered, hydrogen sulfide is added to the filtrate, the mixture is filtered, and the filtrate is concentrated. The concentrate is purified with methylene chloride-petroleum ether, giving 12.5 g (yield 90%) of dimethyl-4-(tetrahydro-2-furanyl)butylsulfonium lactate (Compound 67).

EXAMPLE 27

The same method as in Example 26 is repeated with the use of appropriate starting-materials. Compounds 66, 72, 77, 86, 88, 93, 95, 96, 98, 103, 109, 115, 117, 118, 119, 124, 125, 126, 129, 130, 132 and 133 are prepared.

EXAMPLE 28

To 100 ml of nitromethane are added 4.14 g of butylpropyl-5-(tetrahydro-2-pyranyl)pentylsulfonium iodide and 3.1 g of silver p-toluenesulfonate, and the mixture is stirred at 40°–50° C. for 3 hours. The reaction mixture is filtered, hydrogen sulfide is added to the filtrate, and the resulting precipitate is filtered off. The filtrate is concentrated, and the concentrate is purified with methylene chloride-ether, giving 4.2 g (yield 91.7%) of butylpropyl-5-(tetrahydro-2-pyranyl)pentylsulfonium p-toluenesulfonate (Compound 112).

EXAMPLE 29

The same method as in Example 28 is repeated with the use of appropriate starting-materials. Compounds 71, 79, 99 and 102 are prepared.

EXAMPLE 30

To 50 ml of ethanol are added 4.35 g of dibenzyl-5-(tetrahydro-2-furanyl)pentylsulfonium bromide and 3.3 g of potassium p-toluenesulfonate, and the mixture is stirred at room temperature for 6 hours. An oily product formed by the addition of ether to the reaction mixture is purified with methylene chloride-ether, giving 4.3 g (yield 81.7%) of dibenzyl-5-(tetrahydro-2-furanyl)pentylsulfonium p-toluenesulfonate (Compound 80).

EXAMPLE 31

Compound 106 is prepared by the same method as in Example 30, but using appropriate starting-materials.

EXAMPLE 32

To 200 ml of methanol are added 8.9 g of ethylmethyl-5-(tetrahydro-2-furanyl)pentylsulfonium bromide and 8.3 g of silver oxide, and the mixture is stirred at room temperature for 5 hours. The reaction mixture is filtered, 6.5 g of cyclohexylsulfamic acid is added to the filtrate, and the solvent is removed. The residue is purified with methylene chloride-ether, giving 10.8 g (90.8%) of ethylmethyl-5-(tetrahydro-2-furanyl)pentylsulfonium cyclohexylsulfamate (Compound 75).

EXAMPLE 33

The same method as in Example 32 is repeated with the use of appropriate starting-materials. Compounds 83, 108 and 114 are prepared.

Given below are examples of pharmaceutical preparations containing compounds of this invention.

Preparation 1: Tablets

Tablets are prepared from the following composition (100 mg per tablet).
Compound 46—5 mg
Crystalline cellulose—35 mg
Lactose—39 mg
Corn starch—15 mg
Hydroxypropyl cellulose—5 mg
Magnesium stearate—1 mg

Preparation 2: Capsules

An encapsulated preparation is formulated from the following composition (350 mg per capsule).
Compound 29—250 mg
Crystalline cellulose—70 mg
Lactose—23 mg
Light silicic anhydride—3.5 mg
Magnesium stearate—3.5 mg

Preparation 3: Particles

A particulate preparation is formulated from the following composition (1000 mg per wrapper).
Compound 1—500 mg
Crystalline cellulose—40 mg
Lactose—200 mg
Corn starch—200 mg
Hydroxypropyl cellulose—50 mg
Magnesium stearate—10 mg

Preparation 4: Granules

A granular preparation is formulated from the following composition (1000 mg per wrapper).
Compound 58—500 mg
Crystalline cellulose—40 mg Corn starch—100 mg
Lactose—300 mg
Hydroxypropyl cellolose—50 mg
Magnesium stearate—10 mg Preparation 5: Syrup A 50 ml quantity of syrup is prepared from the following composition.
Compound 50—5.0 g
Sucrose—32.5 g
Ethyl p-hydroxybenzoate—2 mg
Butyl p-hydroxybenzoate—3 mg
Coloring agent—small amount
Flavor—small amount
Purified water—q.s. 50 ml Preparation 6: Suppositories Suppositories are prepared from the following composition (8.5 g per piece)
Compound 29—1.0 g
Fatty acid glyceride—7.5 g
(available under the trade mark "Witepsol W-35", product of Dynamit Nobel A. G., West Germany.)

Preparation 7: Injection solution

An injection solution is prepared from the following composition (1 ml per ampule).
Compound 28—10 mg
Sodium chloride—8 mg
Distilled water for injection—q.s. 1 ml Compounds of this invention were tested for pharmacological activities and for acute toxicity, with the following results.

(1) Effect on humoral response

Ten male BALB/C mice in each group, weighing 25–30 g, were intravenously injected with $1 \times 10^7$ sheep red blood cells on day 0. A solution of the compound in physiological saline was injected intraperitoneally at the dose shown in Table 1 below from day 0 to day 4.

On day 5, spleen hemolytic plaque forming cells were counted by the technique of Jerne et al (Science, 140, 405, 1963) modified by Cunningham et al (Immunology, 14, 599, 1968).

As shown in Table 1, Compound 1 achieve significant increases in the number of hemolytic plaque forming cells at the doses of 2.5 mg/kg and 40 mg/kg.

TABLE 1

| Compound No. | Dose (mg/kg/day) | Cell count/spleen | Increase % |
|---|---|---|---|
| Compound 1 | 2.5 | 322 ± 75.2 | 52.6 |
| | 10 | 285 ± 113.5 | 35.1 |
| | 40 | 392 ± 91.4 | 85.8 |
| Saline (control) | — | 211 ± 80.2 | — |

(2) Effect on a cell-mediated response

Ten male BALB/C mice in each group, weighing in 20–25 g, were used. Mice were immunized by applying the skin of the clipped abdomen with 0.1 ml of 7% picryl chloride in absolute alcohol on day 0, and challenge was with 0.02 ml of 1% picryl chloride in olive oil applied to the ear on day 7. The ear was measured again 24 hours later by a dial thickness gauge. A solution of the compound in water was orally administered at the dose shown in Table 2 below daily for seven consecutive days starting with day 1. As shown in Table 2, Compound 1 and Compound 29 augment the delayed hypersensitivity response.

TABLE 2

| Compound No. | Dose (mg/kg/day) | Increase of swelling ($\times 10^{-4}$) | Increase relative to control group (%) |
|---|---|---|---|
| Comp. 1 | 20 | 34.2 ± 6.0 | −3.4 |
| | 100 | 50.8 ± 13.4 | 43.5 |
| | 500 | 39.3 ± 9.8 | 11.0 |
| Comp. 29 | 20 | 44.8 ± 9.5 | 26.0 |
| | 100 | 47.9 ± 13.2 | 35.3 |
| | 500 | 31.3 ± 13.5 | −11.6 |
| Distilled water (control) | — | 35.4 ± 9.8 | — |

(3) Acute toxicity test

Male ddy mice weighing 20 g were used. A solution of the compound in physiological saline was injected intravenously. The dose lethal to 50% of mice was determined by the up-down method. The results are shown in Table 3.

TABLE 3

| Compound No. | LD 50 (mg/kg) |
|---|---|
| Compound 1 | 130 |
| Compound 12 | 90 |
| Compound 27 | 94 |
| Compound 29 | 131 |
| Compound 46 | 13.2 |
| Compound 50 | 135 |
| Compound 58 | 80 |

We claim:

1. A pharmaceutical composition comprising 0.5 mg to 5,000 mg of a sulfonium compound of the Formula (I)

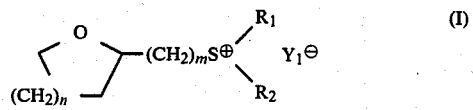

wherein $R_1$ and $R_2$ are each alkyl, cycloalkyl, cycloporpylmethyl, alkylene-2-tetrahydrofuranyl, alkylene-2-tetrahydropyranyl, alkenyl, phenyl which may be substituted with aklyl, alkoxy or halogen, aralkyl which may be substituted with alkyl, alkoxy or halogen on the benzene ring, or benzoyloxyethyl, $Y_1$ is halogen, or an inorganic acid residue or organic acid residue, n is 1 or 2, and m is an integer of 1 to 15, together with a pharmaceutically acceptable carrier therefor.

2. Composition of claim 1, wherein m is an integer of 1 to 5.

3. Composition of claim 1, wherein one of $R_1$ and $R_2$ is alkyl.

4. Composition of claim 1, wherein $R_1$ and $R_2$ are each alkyl.

5. Composition of claim 4, wherein $R_1$ and $R_2$ are each methyl.

6. Composition as defined in claim 1, wherein $Y_1$ is an organic sulfonic acid residue, an organic carboxylic acid residue or halogen.

7. Composition as defined in claim 6, wherein the organic sulfonic acid is toluenesulfonic acid, picrylsulfonic acid, cyclohexylsulfamic acid or methanesulfonic acid.

8. Composition as defined in claim 6, wherein the organic carboxylic acid is an unsaturated dibasic acid.

9. Composition as defined in claim 1, wherein $R_1$ and $R_2$ are each alkyl, m is an integer of 1 to 5, and $Y_1$ is an organic sulfonic acid residue.

10. A method for stimulating the immune response in a mammal, said method comprising administering to said mammal an immunity stimulating effective amount of a sulfonium compound of the formula (I)

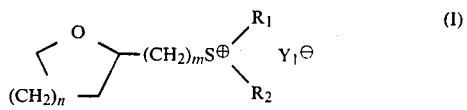

wherein $R_1$ and $R_2$ are each alkyl, cycloalkyl, cyclopropylmethyl, alkylene-2-tetrahydrofuranyl, alkylene-2-tetrahydropyranyl, alkenyl, phenyl which may be substituted with alkyl, alkoxy or halogen, aralkyl which may be substituted with alkyl, alkoxy or halogen on the benzene ring, or benzoyloxyethyl, $Y_1$ is halogen, or an inorganic acid residue or organic acid residue, n is 1 or 2, and m is an integer of 1 to 15, together with a pharmaceutically acceptable carrier therefor.

11. Method of claim 10, wherein m is an integer of 1 to 5.

12. Method of claim 10, wherein one of $R_1$ and $R_2$ is alkyl.

13. Method of claim 10, wherein $R_1$ and $R_2$ are each alkyl.

14. Method of claim 10, wherein $R_1$ and $R_2$ are each methyl.

15. Method of claim 10, wherein $Y_1$ is an organic sulfonic acid residue, an organic carboxylic acid residue or halogen.

16. Method as defined in claim 15, wherein the organic sulfonic acid is toluenesulfonic acid, picrylsulfonic acid, cyclohexylsulfamic acid or methanesulfonic acid.

17. Method as defined in claim 15, wherein the organic carboxylic acid is an unsaturated dibasic acid.

18. Method as defined in claim 10, wherein $R_1$ and $R_2$ are each alkyl, m is an integer of 1 to 5, and $Y_1$ is an organic sulfonic acid residue.

* * * * *